(12) United States Patent
Mayo et al.

(10) Patent No.: US 9,555,051 B2
(45) Date of Patent: Jan. 31, 2017

(54) VESICULAR FORMULATIONS

(71) Applicant: Sequessome Technology Holdings Limited, Valletta (MT)

(72) Inventors: John Mayo, London (GB); William Henry, London (GB)

(73) Assignee: Sequessome Technology Holdings Limited, Valletta (MT)

( * ) Notice: Subject to any disclaimer, the term of this patent is extended or adjusted under 35 U.S.C. 154(b) by 0 days.

(21) Appl. No.: 14/388,469

(22) PCT Filed: Mar. 28, 2013

(86) PCT No.: PCT/EP2013/056694
§ 371 (c)(1),
(2) Date: Sep. 26, 2014

(87) PCT Pub. No.: WO2013/144289
PCT Pub. Date: Oct. 3, 2013

(65) Prior Publication Data
US 2015/0057249 A1    Feb. 26, 2015

(30) Foreign Application Priority Data

Mar. 29, 2012   (GB) .................................. 1205642.0

(51) Int. Cl.
| | | |
|---|---|---|
| *A61K 31/688* | (2006.01) | |
| *A61K 9/107* | (2006.01) | |
| *A61K 9/06* | (2006.01) | |
| *A61K 9/00* | (2006.01) | |
| *A61K 47/10* | (2006.01) | |
| *A61K 47/24* | (2006.01) | |
| *A61K 47/26* | (2006.01) | |
| *A61K 31/685* | (2006.01) | |
| *A61K 31/7032* | (2006.01) | |
| *A61K 31/683* | (2006.01) | |
| *A61K 47/32* | (2006.01) | |

(52) U.S. Cl.
CPC ........... *A61K 31/688* (2013.01); *A61K 9/0014* (2013.01); *A61K 9/06* (2013.01); *A61K 9/107* (2013.01); *A61K 31/683* (2013.01); *A61K 31/685* (2013.01); *A61K 31/7032* (2013.01); *A61K 47/10* (2013.01); *A61K 47/24* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 5,015,483 A | 5/1991 | Haynes et al. | |
| 5,498,420 A | 3/1996 | Edgar et al. | |
| 5,498,607 A | 3/1996 | Hsia et al. | |
| 5,853,753 A | 12/1998 | Maierhofer et al. | |
| 6,165,500 A | 12/2000 | Cevc | |
| 6,191,121 B1 | 2/2001 | Perricone | |
| 6,248,728 B1 | 6/2001 | Koo | |
| 6,534,070 B1 * | 3/2003 | Franke | A61K 9/0014 424/400 |
| 7,175,850 B2 | 2/2007 | Cevc | |
| 7,476,432 B2 | 1/2009 | Pringle et al. | |
| 7,544,375 B1 | 6/2009 | Bellin et al. | |
| 7,867,480 B1 | 1/2011 | Cevc et al. | |
| 2002/0012680 A1 | 1/2002 | Patel | |
| 2003/0064948 A1 | 4/2003 | Fahr et al. | |
| 2003/0099694 A1 | 5/2003 | Cevc et al. | |
| 2003/0161867 A1 | 8/2003 | Lu et al. | |
| 2004/0071767 A1 | 4/2004 | Cevc | |
| 2004/0105881 A1 | 6/2004 | Cevc | |
| 2005/0123593 A1 | 6/2005 | Thompson et al. | |
| 2007/0042008 A1 | 2/2007 | Kane et al. | |
| 2007/0224256 A1 | 9/2007 | Bolton et al. | |
| 2007/0238708 A1 | 10/2007 | Mandel et al. | |
| 2008/0095722 A1 | 4/2008 | Cevc et al. | |
| 2008/0268042 A1 | 10/2008 | Feuerstein et al. | |
| 2009/0060990 A1 | 3/2009 | Cevc et al. | |
| 2009/0324727 A1 | 12/2009 | Roca | |
| 2010/0098749 A1 | 4/2010 | Barenholz et al. | |
| 2010/0105139 A1 | 4/2010 | Spanjaard | |
| 2010/0130611 A1 | 5/2010 | Feuerstein et al. | |
| 2010/0197621 A1 | 8/2010 | Henry et al. | |
| 2012/0045405 A1 | 2/2012 | Gilman et al. | |
| 2014/0100191 A1 | 4/2014 | Kroon et al. | |
| 2015/0065461 A1 | 3/2015 | Garraway et al. | |
| 2015/0125407 A1 | 5/2015 | Henry et al. | |
| 2015/0132349 A1 | 5/2015 | Garraway et al. | |

FOREIGN PATENT DOCUMENTS

| | | |
|---|---|---|
| CN | 1826123 A | 8/2006 |
| EP | 0220797 A2 | 5/1987 |
| EP | 0475160 | 8/1991 |
| EP | 1551370 B1 | 4/2004 |
| EP | 2382994 A1 | 11/2011 |
| ES | 2107668 T3 | 12/1997 |
| JP | 4-55167 B2 | 9/1992 |
| JP | 7-206879 A | 8/1995 |
| JP | 8-509202 A | 10/1996 |
| JP | 11-139956 A | 5/1999 |

(Continued)

OTHER PUBLICATIONS

Lahey Hospital & Medical Center. "Lecithin". 2016.*
PCT International Search Report and Written Opinion for PCT/US2010/046245, dated Oct. 1, 2010, 29 Pages.
PCT International Preliminary Report on Patentability for PCT/US2010/046245, dated Oct. 24, 2011, 30 Pages.
PCT International Search Report and Written Opinion for PCT/IB2010/001557, dated Jun. 6, 2011, 12 Pages.
PCT International Search Report and Written Opinion for PCT/EP2013/057742, dated May 21, 2013.

(Continued)

*Primary Examiner* — Anna Pagonakis
(74) *Attorney, Agent, or Firm* — Fenwick & West LLP

(57) ABSTRACT

The present invention relates to vesicular formulations for the treatment of rosacea. It also relates to a method of treating rosacea comprising administering a vesicular formulation according to the invention.

10 Claims, No Drawings

(56) References Cited

FOREIGN PATENT DOCUMENTS

| | | | |
|---|---|---|---|
| JP | 11-507369 A | 6/1999 |
| JP | 2001-523723 A | 11/2001 |
| JP | 2004-131432 A | 4/2004 |
| JP | 2005-515242 A | 5/2005 |
| JP | 2005-179313 A | 7/2005 |
| JP | 2006-525368 A | 11/2006 |
| JP | 2006-528136 A | 12/2006 |
| JP | 2007-269720 A | 10/2007 |
| JP | 2008-127327 A | 6/2008 |
| JP | 2009-506120 A | 2/2009 |
| JP | 2009-256331 A | 11/2009 |
| WO | WO-87/01938 A1 | 4/1987 |
| WO | WO-98/17255 A1 | 4/1998 |
| WO | WO-00/12060 A1 | 3/2000 |
| WO | WO-01/76555 A2 | 10/2001 |
| WO | WO-03/077861 A2 | 9/2003 |
| WO | WO-2004/006954 A2 | 1/2004 |
| WO | WO-2005/007169 A2 | 1/2005 |
| WO | WO-2006/086992 A2 | 8/2006 |
| WO | WO-2008/077641 A1 | 7/2008 |
| WO | WO-2008/156646 A1 | 12/2008 |
| WO | WO-2009/093193 A2 | 6/2009 |
| WO | WO-2009/106338 A2 | 9/2009 |
| WO | 2010140061 | 12/2010 |
| WO | 2011022707 | 2/2011 |
| WO | WO-2011/162802 A1 | 12/2011 |
| WO | WO-2013/153221 A1 | 10/2013 |
| WO | WO-2013/171131 A1 | 11/2013 |
| WO | WO-2013/171132 A1 | 11/2013 |
| WO | WO-2015/014965 A1 | 2/2015 |

OTHER PUBLICATIONS

PCT International Search Report and Written Opinion for PCT/EP2013/059741, dated Jul. 23, 2013, 9 Pages.

PCT International Search Report and Written Opinion for PCT/EP2013/059740, dated Sep. 20, 2013, 19 Pages.

PCT International Search Report and Written Opinion for PCT/EP2014/066545, dated Oct. 15, 2014, 15 Pages.

Cevc, G., "Transfersomes, Liposomes and Other Lipid Suspensions on the Skin: Permeation Enhancement, Vesicle Penetration, and Transdermal Drug Delivery," Critical Reviews in Therapeutic Drug Carrier Systems, 1996, pp. 257-388, vol. 13, Nos. 3 and 4.

Cevc, G., et al., "Ultraflexible vesicles, Transfersomes, have an extremely low pore penetration resistancde and transport therapeutic amounts of insulin across the intact mammalian skin," Biochemica et Biophysica Acta, 1998, pp. 201-215, vol. 1368.

Dieppe, P., et al., "Pathogenesis and management of pain in osteoarthritis," The Lancet, 2005, pp. 965-973, vol. 365.

Bayer: Bepanthen-Spray Mousse Rafraichissant (patient information leaflet), Dec. 10, 2007, XP002636839.

Kawano, T., et al., "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis," Arthritis & Rheumatism, 2003, pp. 1923-1929, vol. 48, No. 7.

Mezei, M., et al., "Dermatitic Effect of Nonionic Surfactants IV: Phospholipid Composition of Normal and Surfactant-Treated Rabbit Skin," Journal of Pharmaceutical Sciences, 1970, pp. 858-861, vol. 59, No. 6.

Sivan, S., et al, "Liposomes Act as Effective Biolubricants for Friction Reduction in Human Synovial Joints," Langmuir, 2010, pp. 1107-1116, vol. 26, No. 2.

Simões, S. I., et al., "Permeabilisation and solubilisation of soybean phosphatidylcholine bilayer vesicles, as membrane models, by polysorbate, Tween 80," European Journal of Pharmaceutical Sciences, 2005, pp. 307-317, vol. 26.

Treede, I., et al., "Anti-Inflammatory Effects of Phosphatidylcholine," The Journal of Biological Chemistry, 2007, pp. 27155-27164, vol. 282, No. 37.

Withdrawal Assessment Report for Diractin; EMEA—European Medicines Agency, Oct. 23, 2008, London, UK, 24 Pages.

United States Office Action, U.S. Appl. No. 13/375,155, dated Jul. 16, 2015, 8 Pages.

United States Office Action, U.S. Appl. No. 13/391,326, dated Jul. 6, 2015, 7 Pages.

United States Office Action, U.S. Appl. No. 14/055,269, dated Jul. 1, 2015, 7 Pages.

Skalko N et al: "Liposomes with Metronidazole for Topical Use: The Choice of Preparation Method and Vehicle", Journal of Liposome Research, Taylor and Francis, Philadelphia, PA, US, vol. 8, No. 2, May 1, 1998.

International Search Report and Written Opinion dated Jun. 21, 2013.

Barthel, H. R., et al., "Randomized Controlled Trial of Diclofenac Sodium Gel in Knee Osteoarthritis," Semin Arthritis Rheum., 2009, pp. 203-212, vol. 39, No. 3.

Cevc, G., et al., "Ultradeformable lipid vesicles can penetrate the skin and other semi-permeable barriers unfragmented. Evidence from double label CLSM experiments and direct size measurements," Biochimica et Biophysica Acta, 2002, pp. 21-30.

Crosasso, P., et al., "Preparation, characterization and properties of sterically stabilized paclitaxel-containing liposomes," Journal of Controlled Release, 2000, pp. 19-30.

Gallarate, M., et al., "Deformable Liposomes as Topical Formulations Containing α-Tocopherol," Journal of Dispersion Science and Technology, 2006, pp. 703-713, vol. 27, No. 5.

Idea AG, "Updates on Diractin® (ketoprofen in Transfersome® gel) status," Oct. 7, 2009, Munich, Germany.

Idea AG, "Multicenter, Randomized, Double-Blind, Placebo- and Active-Controlled Study of Safety and Efficacy of Two Dosages of Epicutaneously Applied Diractin® (Ketoprofen in Transfersome® Gel) for the Treatment of Osteoarthritis of the Knee," In: ClinicalTrials.gov [Internet], Bethesda (US): National Library of Medicine (US), Apr. 26, 2016, Available from: https://clinicaltrials.gov/archive/NCT00716547/2009_01_20.

Knee Joint Picture at www.medicinenet.com/image-collection/knee_joint_picture/picture.htm (retrieved from the Internet May 4, 2016).

Osteoarthritis Symptoms at www.mayoclinic.org/diseases-conditions/osteoarth ritis/symptoms-causes/dxc-201 98250?p=1(retrieved from the Internet May 4, 2016).

Roth, S. H., et al., "Efficacy and Safety of a Topical Diclofenac Solution (Pennsaid) in the Treatment of Primary Osteoarthritis of the Knee," Arch Intern Med., 2004, pp. 2017-2023, vol. 164, No. 18.

Sumida, Y., "Application of a Liposome Technique to Cosmetics," Membrane, 1998, pp. 144-152, vol. 24, No. 3. (English abstract).

United States Office Action, U.S. Appl. No. 14/400,866, dated Mar. 11, 2016, 6 Pages.

United States Office Action, U.S. Appl. No. 14/391,754, dated May 11, 2016, 18 Pages.

United States Office Action, U.S. Appl. No. 14/400,874, dated May 13, 2016, 18 Pages.

\* cited by examiner

VESICULAR FORMULATIONS

CROSS-REFERENCE TO RELATED APPLICATION

This application is the 35 U.S.C. §371 national stage of, and claims priority to and the benefit of, PCT application PCT/EP2013/056694, filed Mar. 28, 2013, which claims priority to and the benefit of GB Application No. 1205642.0, filed on Mar. 29, 2012, herein incorporated by reference in its entirety.

The present invention relates to vesicular formulations for the treatment of rosacea. It also relates to a method of treating rosacea comprising administering a vesicular formulation according to the invention.

The present invention relates to formulations of water, phospholipids and surfactants and to the use of such formulations for the treatment of rosacea where these components may form vesicles or micelles or aggregates within the vesicular formulation.

Rosacea is a chronic condition. The condition is characterised by facial erythma (redness). The condition typically begins as flushing or redness on the face but can also affect the neck, chest, ears and scalp. There are four sub-types of rosacea: erythematotelangiectatic rosacea, semi-permanent or permanent flushing and telangiectesia, papulopustular rosacea characterised by papules and/or pustules, phymatous rosacea causing thickening of the skin especially around the nose, and ocular rosacea characterised by red and irritated eyes. It primarily affects Caucasians, with three times as many women being affected than men. The symptoms of rosacea should not be confused with inflammation caused by dermatological conditions such as acne. The pathophysiology of rosacea is poorly understood. Manifestation is thought to arise from cutaneous vasomotor instability.

It is almost entirely a cosmetic condition which nevertheless causes considerable distress for sufferers of the condition. There is no known effective treatment. The use of topical steroids to treat the condition is reported to aggravate the condition. There is a need to provide treatment for rosacea.

U.S. Pat. No. 6,165,500 describes a preparation for the application of agents which are provided with membrane-like structures consisting of one or several layers of amphiphilic molecules, or an amphiphilic carrier substance, in particular for transporting the agent into and through natural barriers such as skin and similar materials. These Transfersomes™ consist of one or several components, most commonly a mixture of basic substances, one or several edge-active substances, and agents.

US Patent Application Publication No. US 2004/0071767 describes formulations of nonsteroidal anti-inflammatory drugs (NSAIDs) based on complex aggregates with at least three amphiphatic components suspended in a pharmaceutically acceptable medium.

US Patent Application Publication No. US 2004/0105881 describes extended surface aggregates, suspendable in a suitable liquid medium and comprising at least three amphiphats (amphiphatic components) and being capable to improve the transport of actives through semi-permeable barriers, such as the skin, especially for the non-invasive drug application in vivo by means of barrier penetration by such aggregates. WO 2010/140061 describes the use of "empty" vesicular formulations for the treatment of deep tissue pain. WO 2011/022707 describes the use of the same "empty" vesicular formulations for treating disorders relating to fatty acid deficiencies and inter alia disorders related to inflammation.

None of these documents disclose or teach the use of vesicular formulations for the treatment of rosacea.

Citation of any reference in this section of the application is not an admission that the reference is prior art to the application. The above noted publications are hereby incorporated by reference in their entirety.

The present invention relates to a vesicular formulation, for use in the treatment of rosacea, comprising one or more phospho or sulpholipids and one or more surfactants. Vesicular formulations are described in WO2011/022707 and WO2010/140061 and throughout this application. The formulation may be a cream, lotion, ointment, gel, solution, spray, lacquer or film forming solution.

The vesicular formulation does not need to contain any known pharmaceutically active ingredient, including a steroid, an antibiotic, including rifaximin, azelaic acid, isotretinoin, antihistamine, mirtazapine, methyl sulfonylmethane or the Galderma product designated CD07805/47. The formulation may not contain any known pharmaceutically active ingredient acknowledged in the prevention or treatment of rosacea.

The present invention also provides a method of treating rosacea, the method comprising administering a formulation according to the invention to a patient in need thereof.

The invention encompasses vesicular formulations comprising one or more phospho or sulpholipids and one or more surfactants that are effective for the delivery of fatty acids and/or phospholipids in the treatment of rosacea. These vesicular formulations are suitable for any method of administration, e g, subcutaneously, topically, or intravenously. The surfactant may be nonionic.

The formulations of the invention are preferably formulated in the absence of any pharmaceutically active agent, i.e., any non-lipid non-surfactant pharmaceutically active agent. The formulations of the invention preferably do not contain any one or more of a steroid, an antibiotic (including rifaximin), azelaic acid, isotretinoin, antihistamine, mirtazapine or methyl sulfonylmethene.

As used herein, the term "formulation" is not meant to imply that the ingredients or components are in combination with a pharmaceutically active agent, i.e. any non-lipid non-surfactant active agent that has received regulatory approval for the treatment of rosacea.

A pharmaceutically active agent is here defined as an agent that has pharmacological, metabolic or immunological activity. This may be defined as being biologically active.

Despite the lack of a recognized pharmaceutically active agent, the vesicles elicit a therapeutic effect, namely the treatment of rosacea. Without being bound by any theory, The Applicant believes that the vesicle components themselves may be responsible for this effect.

The vesicular formulation of the invention may be able (without wishing to be bound by theory) to achieve its function through the unique properties of multi-layer vesicles, bilayer vesicles, micelles or aggregates composed of surfactant and lipid ("vesicles"), such as soy phosphatidylcholine. The uniqueness of the vesicles derives from the inclusion in the formulation of a specific amount of surfactant, which modifies the phospholipid membrane to such an extent that the resulting vesicles are in a permanent liquid crystalline state and, since the surfactant also confers membrane stability, the vesicles are ultra deformable and stable (have reduced rigidity without breaking).

The vesicular formulation forms into vesicles suspended in an aqueous buffer that is applied, for example, topically. The vesicles are highly hydrophilic and this property, together with their ultra deformability, is key to their ability to be transported across the skin. When the formulation of the invention is applied to the skin and allowed to dry, the rehydration driving force of the vesicles combined with their deformability give rise to movement of the vesicles to areas of higher water content on and below the skin permeability barrier. This drives their movement through skin pores and intracellular gaps. The specific ratio of lipid to surfactant facilitates transdermal delivery of vesicles.

Once they pass through the skin, the vesicles of the invention (sometimes referred to as "Deformasomes") eventually present as intact vesicles. Efficient clearance of vesicles does not occur via the cutaneous blood microvasculature (capillaries) owing to their relatively large size, but they are hypothesised to be transported with the interstitial fluid into other and/or deeper tissues below the site of dermal application. A number of clinical studies conducted with vesicles of the invention labeled with a marker molecule (terbinafine) showed that the vesicles did not enter the vasculature because, following topical application, high concentrations of the marker molecule were observed locally with minimal systemic absorption (at or near the level of detection).

Without wishing to be bound by theory, it is thought that the vesicles may physically block gaps in the endothelium and thereby prevent capillary leakage, and thus reduce redness and thread veins that are associated with rosacea.

In one embodiment, the invention provides a pharmaceutical package or kit comprising one or more containers filled with the formulation of the invention, and instructions for administration of the formulation to a patient or subject in need thereof for the treatment of rosacea. In various embodiments, the container comprises a formulation formulated as a suspension, emulsion, gel, cream, lotion, spray, film forming solution or lacquer. The invention provides packages or kits that can be used in any of the above-described methods.

In one embodiment, the invention comprises a method for the treatment of rosacea, wherein the vesicular formulations of the invention are administered over a period of one or more weeks, for example for at least five weeks, six weeks, seven weeks, eight weeks, nine weeks, ten weeks, eleven weeks, or twelve weeks, sixteen weeks, twenty four weeks, four months, six months, eight months, ten months, one year, two or more years, or indefinitely.

The invention comprises, in a further embodiment, the vesicular formulations of the invention for use in the treatment of erythema associated with rosacea.

A further embodiment includes the use of the vesicular formulations of the invention for use in the treatment of thread veins associated with rosacea.

In one embodiment, the formulations of the invention comprise one or more phospho or sulpholipids and one or more surfactants. The surfactant may be nonionic.

In one embodiment, a 0.1 to 10 gram dose of the formulation of the invention is administered to the patient. The dose may be 1 to 10 gram, or 1 to 5 gram or about 1 gram, 2 gram, 3 gram, 4 gram, 5 gram, 6 gram, 7 gram, 8 gram, 9 gram or 10 gram. In some embodiments, the dose is measured as the total weight of the Deformasome. In some embodiments, the dose is measured as the total weight of the lipid(s) and surfactant(s) in the Deformasome. The dose may be administered once or twice daily for the treatment of rosacea. The dose may be administered once, twice, three, four, five, six, or seven times per week in accordance with the invention. The dose may be administered every day, every other day, or two to three times a week in accordance with the invention.

In some embodiments, the lipid in the pharmaceutical composition is a phospholipid. In some embodiments, the second lipid is a lysophospholipid. In some embodiments, the surfactant is a non-ionic surfactant.

In some embodiments, the compositions of the invention form vesicles or other extended surface aggregates (ESAs), wherein the vesicular preparations have improved permeation capability through the semi-permeable barriers, such as skin. The adaptability and deformability of the vesicles allow the vesicles to penetrate beneath the skin to the muscle and the joint itself, however, the size of the vesicle prevents penetration into the vasculature and as a result prevents systemic delivery. While not to be limited to any mechanism of action, the formulations of the invention are able to form vesicles characterized by their deformability and/or adaptability. The adaptability or deformability of the vesicles may be determined by the ability of the vesicles to penetrate a barrier with pores having an average pore diameter that is smaller than the average vesicle diameter before the penetration.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The invention can be used on animal which suffers from the condition of rosacea.

As used herein, a "sufficient amount." "amount effective to" or an "amount sufficient to" achieve a particular result refers to an amount of the formulation of the invention is effective to produce a desired effect, which is optionally a therapeutic effect (i.e., by administration of a therapeutically effective amount). Alternatively stated, a "therapeutically effective" amount is an amount that provides some alleviation, mitigation, and/or decrease in at least one clinical symptom. Clinical symptoms associated with the disorder that can be treated by the methods of the invention are well-known to those skilled in the art. Further, those skilled in the art will appreciate that the therapeutic effects need not be complete or curative, as long as some benefit is provided to the subject. For example, a "sufficient amount" or "an amount sufficient to" can be an amount that is effective to treat the symptoms of rosacea.

As used herein, the terms "treat", "treating" or "treatment of mean that the severity of a subject's condition is reduced or at least partially improved or ameliorated and/or that some alleviation, mitigation or decrease in at least one clinical symptom is achieved and/or there is an inhibition or delay in the progression of the condition and/or delay in the progression of the onset of disease or illness. The terms "treat", "treating" or "treatment of also means managing the disease state.

As used herein, the term "pharmaceutically acceptable" when used in reference to the formulations of the invention denotes that a formulation does not result in an unacceptable level of irritation in the subject to whom the formulation is administered. Preferably such level will be sufficiently low to provide a formulation suitable for approval by regulatory authorities.

As used herein with respect to numerical values, the term "about" means a range surrounding a particular numeral value which includes that which would be expected to result from normal experimental error in making a measurement. For example, in certain embodiments, the term "about" when used in connection with a particular numerical value means +−20%, unless specifically stated to be +−1%, +−2%, +−3%, +−4%, +−5%, +−10%. +−15%, or +−20% of the numerical value.

The term "alkyl" refers to a linear or branched saturated monovalent hydrocarbon radical, wherein the alkyl may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl". Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. It is understood in the chemical arts, that the use of the longer chains described herein may be appropriate, or appropriate only in limited amounts, within a molecule so that the properties of the resulting molecule (such as solubility) are appropriate for the use. Thus, while those in the art may use the above longer length alkyl substituents they will be used only when appropriate to provide the desired function.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents Q as described herein.

The term "heteroaryl" refers to a monocyclic aromatic group and/or multicyclic aromatic group that contain at least one aromatic ring, wherein at least one aromatic ring contains one or more heteroatoms independently selected from O, S. and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyi. furanyl. thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. In certain embodiments, heteroaryl may also be optionally substituted with one or more substituents Z as described herein.

The term "alkenyl" as used herein refers to —C(O)-alkenyl. The term "alkenyl" refers to a linear or branched monovalent hydrocarbon radical, which contains one or more, in one embodiment, one to five, carbon-carbon double bonds. The alkenyl may be optionally substituted with one or more substituents Z as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 30 ($C_{2-30}$), 2 to 24 ($C_{2-24}$), 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 30 ($_{3-30}$), 3 to 24 ($C_{3-24}$). 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenoyl is mono-alkenoyl, which contains one carbon-carbon double bond. In certain embodiments, the alkenoyl is di-alkenoyl, which contains two carbon-carbon double bonds. In certain embodiments, the alkenoyl is poly-alkenoyl, which contains more than two carbon-carbon double bonds.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, [beta]-carbolinyl, carbazolyl, chromanyl, chromonyl, cinnolinyl, coumarinyl, decahydroisoquinolinyl, dibenzofuranyl, dihydrobenzisothiazinyl. dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydro furanyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl. quinolinyl, quinoxalinyl, quinuclidinyl, tetrahydrofuryl, tetrahydro furanyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyL triazinyl, triazolyl, and 1,3,5-trithianyl. In certain embodiments, heterocyclic may also be optionally substituted with one or more substituents Z as described herein. The term "halogen", "halide" or "halo" refers to fluorine, chlorine, bromine, and/or iodine.

The term "optionally substituted" is intended to mean that a group, including alkyl, alkenyl, alkynyl, cycloalkyl, aryl, aralkyl, heteroaryl, and heterocyclyl, may be substituted with one or more substituents Z, in one embodiment, one, two, three or four substituents Z, where each Z is independently selected from the group consisting of cyano, halo, OXO, nitro, $C_{1-6}$ alkyl, halo-$C_{1-6}$ alky!, $C_{2-6}$ alkenyl, $C_{2-6}$ alkynyl, $C_{3-7}$ cycloalkyl, $C_{6-14}$ aryl, $C_{7-14}$ aralkyl, heteroaryl, heterocyclyl, —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$. —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^f$, —N$R^e$C(O)O$R^f$, —N$R^e$C(O)N$R^f R^g$, —N$R^e$C(=N$R^h$)N$R^f R^g$, —N$R^e$S(O)$R^f$, —N$R^e$S(O)$_2 R^f$, —N$R^e$ S(O)N$R^f R^g$, —N$R^e$S(O)$_2$N$R^f R^g$, —S$R^e$, —S(O)$R^e$, and —S(O)$_2 R^e$, and —S(O)$_2$N$R^f R^g$, wherein each $R^e$, $R^f$, $R^g$, and $R^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, or heterocyclyl; or $R^f$ and $R^g$ together with the N atom to which they are attached form heterocyclyl.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

In accordance with this disclosure, the term "comprising" is inclusive or open-ended and docs not exclude additional, unrecited elements or method steps; the term "consisting of" excludes any element, step, or ingredient not specified; and the term "consisting essentially of" excludes any element, step, or ingredient that materially changes a basic characteristic of the invention.

In some embodiments, the formulation of the invention provided herein comprise at least one lipid, preferably a phospho or sulpholipid, at least one surfactant, preferably a nonionic surfactant, optionally suspended in a pharmaceutically acceptable medium, preferably an aqueous solution, preferably having a pH ranging from 3.5 to 9.0, preferably from 4 to 7.5. The formulation of the invention may optionally contain buffers, antioxidants, preservatives, microbicides. antimicrobials, emollients, co-solvents, and/or thickeners. In some embodiments, the formulation of the invention comprises a mixture of more than one lipid, preferably more than one phospholipid. In some embodiments, the formulation of the invention consists essentially of at least one lipid, preferably a phospholipid, at least one surfactant, preferably a nonionic surfactant, a pharmaceutically acceptable carrier, and optionally buffers, antioxidants, preservatives, microbicides, antimicrobials, emollients, co-solvents, and/or thickeners. In some embodiments, the formulation of the invention consists of at least one lipid, preferably a phospholipid, at least one surfactant, preferably a nonionic surfactant, a pharmaceutically acceptable carrier, and one or more of the following: buffers, antioxidants, preservatives, microbicides, antimicrobials, emollients, co-solvents, and thickeners.

In the sense of this disclosure, a "lipid" is any substance, which has properties like or similar to those of a fat. As a rule, it has an extended apolar group (the "chain", X) and generally also a water-soluble, polar hydrophilic part, the "head" group (Y) and has the basic Formula I:

$$X—Y_n \qquad (I)$$

wherein n is equal to or larger than zero.

Lipids with n=0 are referred to as apolar lipids and lipids with n>1 are referred to as polar lipids. In this sense, all amphophilic substances, including, but not limited to glycerides, glyccrophospholipids, glycerophosphinolipids, glycerophosphonolipids, sulfolipids, sphingolipids, isoprenoid lipids, steroids or sterols and carbohydrate-containing lipids can generally be referred to as lipids, and are included as such in this disclosure. A list of relevant lipids and lipid related definitions is provided in EP 0 475 160 Al (see, e.g. p. 4, 1. 8 to p. 6, 1. 3) and U.S. Pat. No. 6,165,500 (see, e.g., col. 6, 1. 10 to col. 7, 1. 58), each incorporated herein by reference in their entirety.

A phospholipid in various embodiments may contain (I) a moiety derived from glycerol or a sphingosine, (2) a phosphate group, and/or (3) simple organic molecule such as choline. A phospholipid as used herein may, for example, be a compound of Formula II:

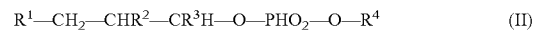
$$R^1—CH_2—CHR^2—CR^3H—O—PHO_2—O—R^4 \qquad (II)$$

wherein $R^1$ and $R^2$ are hydrogen, OH, an alkyl group, an aliphatic chain, an aliphatic chain derived from a fatty acid or a fatty alcohol: provided however that $R^1$ and $R^2$ cannot both be hydrogen, OH or a C1-C3 alkyl group; In some embodiments $R^1$ and $R^2$ are independently, an aliphatic chain, most often derived from a fatty acid or a fatty alcohol; $R^3$ generally is a hydrogen.

The OH-group of the phosphate is a hydroxyl radical or hydro xyl anion (i.e. hydroxide) form, dependent on degree of the group ionization. Furthermore, $R^4$ may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group.

A sphingophospholipid is, for example, a compound of Formula IIB:

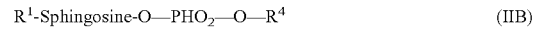
$$R^1\text{-Sphingosine-O}—PHO_2—O—R^4 \qquad (IIB)$$

wherein $R^1$ is a fatty-acid attached via an amide bond to the nitrogen of the sphingosine and $R^4$ has the meanings given under Formula II.

A lipid preferably is a substance of formulae II or HB, wherein $R^1$ and/or $R^2$ are acyl or alkyl, n-hydroxyacyl or n-hydroxyalkyl, but may also be branched, with one or more methyl groups attached at almost any point of the chain;

usually, the methyl group is near the end of the chain (iso or anteiso). The radicals $R^1$ and $R^2$ may moreover either be saturated or unsaturated (mono-, di- or poly-unsaturated). $R^3$ is hydrogen and $R^4$ is 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer, may be considered as well for making the formulations of the disclosure.

A phospholipid is, for example, a compound of Formula IIC as described in WO2011/022707, wherein $R^1$ and $R^2$ are independently an acyl group, alkyl group, n-hydroxyacyl group, or n-hydroxyalkyl group, most often derived from a fatty acid or a fatty alcohol, wherein $R^1$ and $R^2$ may also be branched, with one or more methyl groups attached at almost any point of the chain: usually, the methyl group is near the end of the chain (iso or anteiso). wherein $R^1$ and $R^2$ cannot both be hydrogen, OH or a $C_1$-$C_3$ alkyl group. The radicals $R^1$ and $R^2$ may moreover either be saturated or unsaturated (mono-, di- or poly-unsaturated). $R^3$ generally is a hydrogen. The OH-group of the phosphate is a hydroxyl radical or hydroxyl anion (i.e. hydroxide) form, dependent on degree of the group ionization. Furthermore. R may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group. $R^4$ may be 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer may be considered as well for making the formulations of the disclosure.

Table 1 lists preferred phospholipids in accordance with one embodiment of the disclosure.

TABLE 1

Bechen(o)yl
Eruca(o)yl
Arachin(o)yl
Gadolen(o)yl
Arachindon(o)yl
Ole(o)yl
Stear(o)yl
Linol(o)yl
Linole(n/o)yl
Palmitole(o)yl
Palmit(o)yl
Myrist(o)yl
Laur(o)yl
Capr(o)yl The preferred lipids in the context of this disclosure are uncharged and form stable, well hydrated bilayers; phosphatidylcholines, phosphatidylethanolamine, and sphingomyelins are the most prominent representatives of such lipids. Any of those can have chains as listed in the Table 1; the ones forming fluid phase bilayers, in which lipid chains are in disordered state, being preferred.

Different negatively charged, i.e., anionic, lipids can also be incorporated into vesicular lipid bilayers. Attractive examples of such charged lipids are phosphatidylglycerols, phosphatidylinositols and, somewhat less preferred, phosphatidic acid (and its alkyl ester) or phosphatidylserine. It will be realized by anyone skilled in the art that it is less commendable to make vesicles just from the charged lipids than to use them in a combination with electro-neutral bilaycr component(s). In case of using charged lipids, buffer composition and/or pH care must selected so as to ensure the desired degree of lipid head-group ionization and/or the desired degree of electrostatic interaction between the, oppositely, charged drug and lipid molecules. Moreover, as with neutral lipids, the charged bilayer lipid components can in principle have any of the chains of the phospholipids as listed in the Table 1. The chains forming fluid phase lipid bilayers are clearly preferred, however, both due to vesicle adaptability increasing role of increasing fatty chain fluidity and due to better ability of lipids in fluid phase to mix with each other.

The fatty acid- or fatty alcohol-derived chain of a lipid is typically selected amongst the basic aliphatic chain types below:

| | | |
|---|---|---|
| Dodecanoic | cis-9-Tetradecanoic | 10-cis,13-cis-Hexadecadienoic |
| Tridecanoic | cis-7-Hexadecanoic | 7-cis,10-cis-Hexadecandienoic |
| Tetradecanoic | cis-9-Hexadecanoic | 7-cis,10-cis,13-cis-Hexadecatrienoic |
| Pentadecanoic | cis-9-Octadecanoic | 12-cis,15-cis-Octadecadienoic |
| Hexadecanoic | cis-11-Octadecanoic | trans-10,trans-12-Octadecadienoic |
| Heptadecanoic | cis-11-Eicosanoic | 9-cis,12-cis,15-cis-Octadecatrienoic |
| Octadecanoic | cis-14-Eicosanoic | 6-cis,9-cis,12-cis-Octadecatrienoic |
| Nonadecanoic | cis-13-Docosanoic | 9-cis,11-trans,13-trans-Octadecatrienoic |
| Eicosanoic | cis-15-Tetracosanoic | 8-trans,10-trans,12-cis-Octadecatrienoic |
| Heneicosanoic | trans-3-Hexadecanoic | 6,9,12,15-Octadecatetraenoic |
| Docosanoic | tans-9-Octadecanoic | 3,6,9,12-Octadecatetraenoic |
| Tricosanoic | trans-11-Octadecanoic | 3,6,9,12,15-Octadecapentaenoic |
| Tetracosanoic | | 14-cis,17-cis-Eicosadienoic |
| | | 11-cis,14-cis-Eicosadienoic |
| | | 8-cis,11-cis-14-cis-Eicosadienoic |
| | | 8-cis,11-cis-14-cis-Eicosadienoic |
| | | 5,8,11all-cis-Eicosatrienoic |
| | | 5,8,11;14-all-cis-Eicosatrienoic |
| | | 8,11,14,17-all-cis-Eicosatetraenoic |
| | | 5,8,11,14,17-all-cis-Eicosatetraenoic |
| | | 13,16-Docosadienoic |
| | | 13,16,19-Docosadienoic |
| | | 10,13,16-Docosadienoic |
| | | 7,10,13,16-Docosadienoic |
| | | 4,7,10,13,16-Docosadienoic |
| | | 4,7,10,13,16,19-Docosadienoic |

Other double bond combinations or positions are possible as well.

Suitable fatty residues can furthermore be branched, for example, can contain a methyl group in an iso or anteiso position of the fatty acid chain, or else closer to the chain middle, as in 10-R-methyloctadecanoic acid or tuberculostearic chain Relatively important amongst branched fatty acids are also isoprenoids, many of which are derived from 3,7,11,15-tetramethylhexadec-trans-2-en-1-ol, the aliphatic alcohol moiety of chlorophyll. Examples include 5,9,13,17-tetramethyloctadecanoic acid and especially 3,7,11,15-tetramethylhexadecanoic (phytanic) and 2,6,10,14-tetramethylpentadecanoic (pristanic) acids. A good source of 4,8,12-trimethyltridecanoic acid are marine organisms. Combination of double bonds and side chains on a fatty residue are also possible.

Alternatively, suitable fatty residues may carry one or a few oxy- or cyclic groups, especially in the middle or towards the end of a chain. The most prominent amongst the later, alicyclic fatty acids, are those comprising a cyclopropane (and sometimes cyclopropene) ring, but cyclohexyl and cycloheptyl rings can also be found and might be useful for purposes of this disclosure. 2-(D)-Hydroxy fatty acids are more ubiquitous than alicyclic fatty acids, and are also important constituents of sphingolipids. Also interesting are 15-hydroxy-hexadecanoic and 17-hydroxy-octadecanoic acids, and maybe 9-hydroxy-octadeca-trans-10,trans-12-dienoic (dimorphecolic) and 13-hydroxy-octadeca-cis-9,trans-11-dienoic (coriolic) acid. Arguably the most prominent hydroxyl-fatty acid in current pharmaceutical use is ricinoleic acid, (D-(−)12-hydroxy-octadec-cis-9 enoic acid, which comprises up to 90% of castor oil, which is also often used in hydrogenated form. Epoxy-, methoxy-, and furanoid-fatty acids are of only limited practical interest in the context of this disclosure.

Generally speaking, unsaturation, branching or any other kind of derivatization of a fatty acid is best compatible with the intention of present disclosure of the site of such modification is in the middle or terminal part of a fatty acid chain. The cis-unsaturated fatty acids are also more preferable than trans-unsaturated fatty acids and the fatty radicals with fewer double bonds are preferred over those with multiple double bonds, due to oxidation sensitivity of the latter. Moreover, symmetric chain lipids are generally better suited than asymmetric chain lipids.

A preferred lipid of the Formula II is, for example, a natural phosphatidylcholine, which used to be called lecithin. It can be obtained from egg (rich in palmitic, C16:0, and oleic, C18:1, but also comprising stearic, C18:0, palmitoleic, C16:1, linolenic, C18:2, and arachidonic, C20:4(M, radicals), soybean (rich in unsaturated C18 chains, but also containing some palmitic radical, amongst a few others), coconut (rich in saturated chains), olives (rich in monounsaturated chains), saffron (safflower) and sunflowers (rich in n-6 linoleic acid), linseed (rich in n-3 linolenic acid), from whale fat (rich in monounsaturated n-3 chains), from primrose or primula (rich in n-3 chains). Preferred, natural phosphatidyl ethanolamines (used to be called cephalins) frequently originate from egg or soybeans. Preferred sphingomyelins of biological origin are typically prepared from eggs or brain tissue. Preferred phosphatidylserines also typically originate from brain material whereas phosphatidylglycerol is preferentially extracted from bacteria, such as E. coli, or else prepared by way of transphosphatidylation, using phospholipase D, starting with a natural phosphatidylcholine. The preferably used phosphatidylinositols are isolated from commercial soybean phospholipids or bovine liver extracts. The preferred phosphatidic acid is either extracted from any of the mentioned sources or prepared using phospholipase D from a suitable phosphatidylcholine.

Furthermore, synthetic phosphatidyl cholines ($R^4$ in Formula II corresponds to 2-trimethylammonium ethyl), and $R^1$ and $R^2$ are aliphatic chains, as defined in the preceding paragraph with 12 to 30 carbon atoms, preferentially with 14 to 22 carbon atoms, and even more preferred with 16 to 20 carbon atoms, under the proviso that the chains must be chosen so as to ensure that the resulting ESAs comprise fluid lipid bilayers. This typically means use of relatively short saturated and of relatively longer unsaturated chains. Synthetic sphingomyelins ($R^4$ in Formula IIB corresponds to 2-trimethylammonium ethyl), and $R^1$ is an aliphatic chain, as defined in the preceding paragraph, with 10 to 20 carbon atoms, preferentially with 10 to 14 carbon atoms per fully saturated chain and with 16-20 carbon atoms per unsaturated chain.

Synthetic phosphatidyl ethanolamines ($R^4$ is 2-aminoethyl), synthetic phosphatidic acids ($R^4$ is a proton) or its ester ($R^4$ corresponds, for example, to a short-chain alkyl, such as methyl or ethyl), synthetic phosphatidyl serines ($R^4$ i-s L- or D-serine), or synthetic phosphatidyl (poly)alcohols, such as phosphatidyl inositol, phosphatidyl glycerol ($R^4$ is L- or D-glycerol) are preferred as lipids, wherein $R^1$ and $R^2$ are fatty residues of identical or moderately different type and length, especially such as given in the corresponding tables given before in the text. Moreover, $R^1$ can represent alkenyl and $R^2$ identical hydroxyalkyl groups, such as tetradecylhydroxy or hexadecylhydroxy, for example, in ditetradecyl or dihexadecylphosphatidyl choline or ethanolamine, $R^2$ can represent alkenyl and $R^2$ hydroxyacyl, such as a plasmalogen ($R^4$ trimethylammonium ethyl), or $R^1$ can be acyl, such as lauryl, myristoyl or palmitoyl and $R^2$ can represent hydroxy as, for example, in natural or synthetic lysophosphatidyl cholines or lysophosphatidyl glycerols or lysophosphatidyl ethanolamines, such as 1-myristoyl or 1-palmitoyllysophosphatidyl choline or —phosphatidyl ethanolamine; frequently, $R^3$ represents hydrogen.

A lipid of Formula JIB is also a suitable lipid within the sense of this disclosure. In Formula IIB, n=1, $R^1$ is an alkenyl group. $R^2$ is an acylamido group. $R^3$ is hydrogen and $R^4$ represents 2-trimethylammonium ethyl (choline group). Such a lipid is known under the name of sphingomyelin.

Suitable lipids furthermore are a lysophosphatidyl choline analog, such as 1-lauroyl-1,3-dihydroxypropane-3-phosphoryl choline, a monoglyceride, such as monoolein or monomyristin, a cerebroside, ceramide polyhexoside, sulfatide, sphingoplasmalogen, a ganglioside or a glyceride, which does not contain a free or esterified phosphoryl or phosphono or phosphino group in the 3 position. An example of such a glyceride is diacylglyceride or 1-alkenyl-1-hydroxy-2-acyl glyceride with any acyl or alkenyl groups, wherein the 3-hydroxy group is etherified by one of the carbohydrate groups named, for example, by a galactosyl group such as a monogalactosyl glycerin.

Lipids with desirable head or chain group properties can also be formed by biochemical means, for example, by means of phospholipases (such as phospholipase A1, A2, B, C and, in particular, D), desaturases, elongases, acyl transferases, etc., from natural or synthetic precursors.

Furthermore, a suitable lipid is any lipid, which is contained in biological membranes and can be extracted with the help of apolar organic solvents, such as chloroform. Aside from the lipids already mentioned, such lipids also include, for example, steroids, such as estradiol, or sterols, such as cholesterol, beta-sitosterol, desmosterol, 7-ketocholesterol or beta-cholestanol, fat-soluble vitamins, such as retinoids, vitamins, such as vitamin A1 or A2, vitamin E, vitamin K, such as vitamin K1 or K2 or vitamin D1 or D3, etc.

The less soluble amphiphilic components comprise or preferably comprise a synthetic lipid, such as myristoleoyl, palmitoleoyl, petroselinyl, petroselaidyl, oleoyl, elaidyl, cis- or trans-vaccenoyl, linolyl, linolenyl, linolaidyl, octadecatetraenoyl, gondoyl, eicosaenoyl, eicosadienoyl. eicosatrienoyl, arachidoyl, cis- or trans-docosaenoyl, docosadienoyl, docosatrienoyl, docosatetraenoyl, lauroyl, tridecanoyl. myristoyl, pentadecanoyl, palmitoyl, heptadecanoyl, stearoyl or nonadecanoyl, glycerophospholipid or corresponding derivatives with branched chains or a corresponding dialkyl or sphingosin derivative, glycolipid or other diacyl or dialkyl lipid.

The more soluble amphiphilic components(s) is/are frequently derived from the less soluble components listed above and, to increase the solubility, substituted and/or complexed and/or associated with a butanoyl, pentanoyl. hexanoyl. heptanoyl, octanoyl, nonanoyl, decanoyl or undecanoyl substituent or several, mutually independent, selected substituents or with a different material for improving the solubility.

A further suitable lipid is a diacyl- or dialkyl-glycerophosphoetha-nolamine azo polyethoxylene derivative, a didecanoylphosphatidyl choline or a diacylphosphoolligomaltobionamide.

In certain embodiments, the amount of lipid in the formulation is from about 1% to about 12%, about 1% to about 10%, about 1% to about 4%, about 4% to about 7% or about 7% to about 10% by weight. In a specific embodiment, the lipid is a phospholipid. In another specific embodiment, the phospholipid is a phosphatidylcholine.

In some embodiments, the lipid in the formulation docs not comprise an alkyl-lysophospholipid. In some embodiments, the lipid in the formulation does not comprise a polyeneylphosphatidylcholine.

The term "surfactant" has its usual meaning A list of relevant surfactants and surfactant related definitions is provided in EP 0 475 160 A1 (see, e.g., p. 6, 1. 5 to p.14. 1.17) and U.S. Pat. No. 6,165,500 (see, e g., col. 7, 1. 60 to col. 19, 1. 64), each herein incorporated by reference in their entirety, and in appropriate surfactant or pharmaceutical Handbooks, such as Handbook of Industrial Surfactants or US Pharmacopoeia, Pharm. Eu. In some embodiments, the surfactants are those described in Tables 1-18 of U.S. Patent Application Publication No. 2002/0012680 A1. published Jan. 31, 2002, the disclosure of which is herein incorporated by reference in its entirety. The following list therefore only offers a selection, which is by no means complete or exclusive, of several surfactant classes that are particularly common or useful in conjunction with present patent application. Preferred surfactants to be used in accordance with the disclosure include those with an HLB greater than 12. The list includes ionized long-chain fatty acids or long chain fatty alcohols, long chain fatty ammonium salts, such as alkyl- or alkenoyl-trimethyl-, -dimethyl- and -methyl-ammonium salts, alkyl- or alkenyl-sulphate salts, long fatty chain dimethyl-aminoxides, such as alkyl- or alkenyl-dimethyl-aminoxides, long fatty chain, for example alkanoyl, dimethyl-aminoxides and especially dodecyl dimethyl-aminoxide, long fatty chain, for example alkyl-N-methylglucamide-s and alkanoyl-N-methylglucamides. such as MEGA-8, MEGA-9 and MEGA-IO, N-long fatty chain-N, N-dimethylglycines, for example N-alkyl-N,N-dimethylglycines, 3-(long fatty chain-dimethylammonio)-alkane-sulphonates, for example 3-(acyidimethylammonio)-alkanesulphonatcs, long fatty chain derivatives of sulphosuccinate salts, such as bis(2-ethylalkyl) sulphosuccinate salts, long fatty chain-sulphobetaines, for example acyl-sulphobetaines, long fatty chain betaines, such as EMPIGEN BB or ZWITTERGENT-3-16, -3-14, -3-12, -3-10, or -3-8, or polyethylcn-glycol-acylphenyl ethers, especially nonaethylen-glycol-octyl-phenyl ether, polyethylene-long fatty chain-ethers, especially polyethylene-acyl ethers, such as nonaethylen-decyl ether, nonaethylen-dodecyl ether or octaethylene-dodecyl ether, polyethyleneglycol-isoacyl ethers, such as octaethyleneglycol-isotridecyl ether, polyethyleneglycol-sorbitane-long fatty chain esters, for example polyethyleneglycol-sorbitane-acyl esters and especially polyoxyethylene-monolaurate (e.g. polysorbate 20 or Tween 20), polyoxyethylene-sorbitan-monooleate (e.g. polysorbate 80 or Tween 80), polyoxyethylene-sorbitan-monolauroleylate, polyoxyethylene-sorbitan-monopetroselinate, polyoxyethylene-sorbitan-monoelaidate, polyoxyethylene-sorbitan-myristoleylate, polyoxyethylene-sorbitan-palmitoleinylate, polyoxyethylene-sorbitan-p-etroselinylate, polyhydroxyethylene-long fatty chain ethers, for example polyhydroxyethylene-acyl ethers, such as polyhydroxyethylene-lauryl ethers, polyhydroxyethylene-myristoyl ethers, polyhydroxyethylene-cetylst-earyl, polyhyd roxyethylene-palmityl ethers, polyhydroxyethylene-oleoyl ethers, polyhydroxyethylene-palmitoleoyl ethers, polyhydroxyethylene-lino-leyl, polyhydroxyethylen-4, or 6, or 8, or 10, or 12-lauryl, miristoyl, palmitoyl, palmitoleyl, oleoyl or linoeyl ethers (Brij series), or in the corresponding esters, polyhydroxyethylen-laurate, -myristate, -palmitate, -stearate or -oleate, especially polyhydroxyethylen-8-stearate (Myrj 45) and polyhydroxyethylen-8-oleate, polyethoxylated castor oil 40 (Cremophor EL), sorbitane-mono long fatty chain, for example alkylate (Arlacel or Span series), especially as sorbitane-monolaurate (Arlacel 20, Span 20), long fatty chain, for example acyl-N-methylglucamides, alkanoyl-N-methylglucamides, especially decanoyl-N-methylglucamide, dodecanoyl-N-methylglucamide, long fatty chain sulphates, for example alkyl-sulphates, alkyl sulphate salts, such as lauryl-sulphate (SDS), oleoyl-sulphate: long fatty chain thioglucosides, such as alkylthioglucosides and especially heptyl-, octyl- and nonyl-beta-D-thioglucopyranoside; long fatty chain derivatives of various carbohydrates, such as pentoses, hexoses and disaccharides, especially alkyl-glucosides and maltosides, such as hexyl-, heptyl-, octyl-, nonyl- and decyl-beta-D-glucopyranoside or D-maltopyranoside; further a salt, especially a sodium salt, of cholate, deoxycholate, glycocholate, glycodcoxycholate, taurodeoxycholate, taurocholate, a fatty acid salt, especially oleate, elaidate, linoleate, laurate, or myristate, most often in sodium form, lysophospholipids, n-octadecylene-glycerophosphatidic acid, octadecylene-phosphorylglycerol, octadecylene-phosphorylserine, n-long fatty chain-glycero-phosphatidic acids, such as n-acyl-glycero-phosphatidic acids, especially lauryl glycero-phosphatidic acids, oleoyl-glycero-phosphatidic acid, n-long fatty chain-phosphoryl glycerol, such as n-acyl-phosphorylglycerol, especially lauryl-, myristoyl-, oleoyl- or palmitoeloyl-phosphorylglycerol, n-long fatty chain-phosphorylserine, such as n-acyl-phosphorylserine, especially lauryl-, myristoyl-, oleoyl- or palmitoeloyl-phosphorylserine, n-tetradecyl-glycero-phosphatidic acid, n-tetradecyl-phosphorylglycerol, n-tetradecyl-phosphorylserine, corresponding-, elaidoyl-, vaccenyl-lysophospholipids, corresponding short-chain phospholipids, as well as all surface active and thus membrane destabilising polypeptides. Surfactant chains are typically chosen to be in a fluid state or at least to be compatible with the maintenance of fluid-chain state in carrier aggregates.

In certain embodiments, the surfactant is a nonionic surfactant. The surfactant may be present in the formulation in about 0.2 to 10%, about 1% to about 10%, about 1% to about 7% or about 2% to 5% by weight. In certain embodiments, the nonionic surfactant is selected from the group consisting of: polyoxyethylene sorbitans (polysobate surfactants), polyhydroxyethylene stearates or polyhydroxyethylene laurylethers (Brij surfactants). In a specific embodiment, the surfactant is a polyoxyethylene-sorbitan-monooleate (e.g. polysorbate 80 or Tween 80) or Tween 20, 40 or 60. In certain embodiments, the polysorbate can have any chain with 12 to 20 carbon atoms. In certain embodiments, the polysorbate is fluid in the formulation, which may contain one or more double bonds, branching, or cyclo-groups.

In some embodiments, the formulations of the invention comprise only one lipid and only one surfactant. In other embodiments, the formulations of the invention comprise more than one lipid and only one surfactant, e.g., two, three, four, or more lipids and one surfactant. In other embodiments, the formulations of the invention comprise only one lipid and more than one surfactant, e.g., two, three, four, or more surfactants and one lipid. In other embodiments, the formulations of the invention comprise more than one lipid and more than one surfactant, e.g., two, three, four, or more lipids and two, three, four, or more surfactants.

The formulations of the invention may have a range of lipid to surfactant ratios. The ratios may be expressed in terms of molar terms (mol lipid/mol surfactant). The molar ratio of lipid to surfactant in the formulations may be from about 1:3 to about 30:1, from about 1:2 to about 30:1, from about 1:1 to about 30:1, from about 2:1 to about 20:1, from about 5:1 to about 30:1, from about 10:1 to about 30:1, from about 15:1 to about 30:1, or from about 20:1 to about 30:1. In certain embodiments, the molar ratio of lipid to surfactant in the formulations of the invention may be from about 1:2 to about 10:1. In certain embodiments, the ratio is from about 1:1 to about 2:1, from about 2:1 to about 3:1, from about 3:1 to about 4:1. from about 4:1 to about 5:1 or from about 5:1 to about 10:1. In certain embodiments, the molar ratio is from about 10.1 to about 30:1, from about 10:1 to about 20:1, from about 10:1 to about 25:1, and from about 20:1 to about 25:1. In specific embodiments, the lipid to surfactant ratio is about 1.0:1.0, about 1.25:1.0, about 1.5/1.0, about 1.75/1.0, about 2.0/1.0, about 2.5/1.0, about 3.0/1.0 or about 4,0/1.0. The formulations of the invention may also have varying amounts of total amount of the following components: lipid and surfactant combined (TA). The TA amount may be stated in terms of weight percent of the total composition. In one embodiment, the TA is from about 1% to about 40%, about 5% to about 30%, about 7.5% to about 15%, about 6% to about 14%, about 8% to about 12%, about 5% to about 10%, about 10% to about 20% or about 20% to about 30%. In specific embodiments, the TA is 6%, 8%, 9%, 10%, 12%, 14%,15% or 20%.

Selected ranges for total lipid amounts and lipid/surfactant ratios (mol/mol) for the formulations of the invention are described in the Table below:

TABLE 2

Total Amount and Lipid to Surfactant Ratios

| TA (and surfactant) (%) | Lipid/Surfactant (mol/mol) |
|---|---|
| 5 to 10 | 1.0 to 1.25 |
| 5 to 10 | 1.25 to 1.72 |
| 5 to 10 | 1.75 to 2.25 |
| 5 to 10 | 2.25 to 3.00 |
| 5 to 10 | 3.00 to 4.00 |
| 5 to 10 | 4.00 to 8.00 |
| 5 to 10 | 10.00 to 13.00 |

TABLE 2-continued

Total Amount and Lipid to Surfactant Ratios

| TA (and surfactant) (%) | Lipid/Surfactant (mol/mol) |
|---|---|
| 5 to 10 | 15.00 to 20.00 |
| 5 to 10 | 20.00 to 22.00 |
| 5 to 10 | 22.00 to 25.00 |
| 10 to 20 | 1.0 to 1.25 |
| 10 to 20 | 1.25 to 1.75 |
| 10 to 20 | 1.25 to 1.75 |
| 10 to 20 | 2.25 to 3.00 |
| 10 to 20 | 3.00 to 4.00 |
| 10 to 20 | 4.00 to 8.00 |
| 10 to 20 | 10.00 to 13.00 |
| 10 to 20 | 15.00 to 20.00 |
| 10 to 20 | 20.00 to 22.00 |
| 10 to 20 | 22.00 to 25.00 |

The formulations of the invention do not comprise a pharmaceutically active agent that has received marketing or regulatory approval in any country for the treatment of rosacea.

The formulations of the invention may optionally contain one or more of the following ingredients: co-solvents, chelators, buffers, antioxidants, preservatives, microbicides, emollients, humectants, lubricants and thickeners. Preferred amounts of optional components are described as follows.

| | Molar (M) or | Rel w %* |
|---|---|---|
| Antioxidant: | | |
| Primary: | | |
| Butylated hydroxyanisole, BHA | | 0.1-8 |
| Butylated hydroxytoluene BHT | | 0.1-4 |
| Thymol | | 0.1-1 |
| Metabisulphite | 1-5 mM | |
| Bisulsphite | 1-5 mM | |
| Thiourea (MW = 76.12) | 1-10 mM | |
| Monothioglycerol (MW = 108.16) | 1-20 mM | |
| Propyl gallate (MW = 212.2) | | 0.02-0.2 |
| Ascorbate (MW = 175.3$^+$ ion) | 1-10 mM | |
| Palmityl-ascorbate | | 0.01-1 |
| Tocopherol-PEG | | 0.5-5 |
| Secondary (chelator) | | |
| EDTA (MW = 292) | 1-10 mM | |
| EGTA (MW = 380.35) | 1-10 mM | |
| Desferal (MW = 656.79) | 0.1-5 mM | |
| Buffer | | |
| Acetate | 30-150 mM | |
| Phosphate | 10-50 mM | |
| Triethanolamine | 30-150 mM | |

*as a percentage of total lipid quantity

The formulations of the invention may include a buffer to adjust the pH of the aqueous solution to a range from pH 3.5 to pH 9, pH 4 to pH 7.5, or pH 6 to pH 7.

Examples of buffers include, but are not limited to. acetate buffers, lactate buffers, phosphate buffers, and propionate buffers.

The formulations of the invention are typically formulated in aqueous media. The formulations may be formulated with or without co-solvents, such as lower alcohols.

The formulations of the invention may comprise at least 20% by weight water. The formulations of the invention may comprise about 20%, about 30%, about 40%, about 50%, about 60% about 70%, about 80%, about 90% by weight water. The formulation may comprise from about 70% to about 80% by weight water.

A "microbicide" or "antimicrobial" agent is commonly added to reduce the bacterial count in pharmaceutical formulations. Some examples of microbicides are short chain alcohols, including ethyl and isopropyl alcohol, chlorbutanol, benzyl alcohol, chlorbenzyl alcohol, dichlorbenzylalcohol, hexachlorophene; phenolic compounds, such as cresol, 4-chloro-m-cresol, p-chloro-m-xylenol. dichlorophene, hexachlorophene, povidon-iodine; parabenes. especially alkyl-parabenes, such as methyl-, ethyl-, propyl-, or butyl-paraben, benzyl paraben; acids, such as sorbic acid, benzoic acid and their salts; quaternary ammonium compounds, such as alkonium salts, e.g., a bromide, benzalkonium salts, such as a chloride or a bromide, cetrimonium salts, e.g., a bromide, phenoalkecinium salts, such as phenododecinium bromide, cetylpyridinium chloride and other salts; furthermore, mercurial compounds, such as phenylmercuric acetate, borate, or nitrate, thiomersal, chlorhexidine or its gluconate, or any antibiotically active compounds of biological origin, or any suitable mixture thereof.

Examples of "antioxidants" are butylated hydroxyanisol (BHA), butylated hydroxytoluene (BHT) and di-tert-butylphenol (LY178002, LY256548, HWA-131, BF-389, CI-986, PD-127443, E-51 or 19, BI-L-239XX, etc.), tertiary butylhydroquinone (TBHQ), propyl gallate (PG), 1-O-hexyl-2,3,5-trimethylhydroquinone (HTHQ); aromatic amines (diphenylamine, p-alkylthio-o-anisidine, ethylenediamine derivatives, carbazol, tetrahydroindenoindol); phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e g. -acetate. -laurate. myristate, -palmitate, -oleate, -linoleate. etc., or an y other suitable tocopheryl-lipoate). tocopheryl-POE-succinate; trolox and corresponding amide and thiocarboxamide analogues; ascorbic acid and its salts, isoascorbate, (2 or 3 or 6)-o-alkylascorbic acids, ascorbyl esters (e.g., 6-o-lauroyl, myristoyl, palmitoyl-, oleoyl, or linoleoyl-L-ascorbic acid, etc.). Also useful are the preferentially oxidised compounds, such as sodium bisulphite, sodium metabisulphite, thiourea; chellating agents, such as EDTA, GDTA, desferral: miscellaneous endogenous defence systems, such as transferrin, lactoferrin, ferritin, cearuloplasmin, haptoglobion, heamopexin, albumin, glucose, ubiquinol-10); enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins). N-acetyl-cystein, mesna. glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid); spice extracts (e.g., from clove, cinnamon, sage, rosemary, mace, oregano, allspice, nutmeg); carnosic acid, carnosol, carsolic acid; rosmarinic acid, rosmaridiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g., U74006F); tryptophan metabolites (e.g., 3-hydroxykynurenine, 3-hydroxyanthranilic acid), and organochalcogenides.

"Thickeners" are used to increase the viscosity of pharmaceutical formulations to and may be selected from selected from pharmaceutically acceptable hydrophilic polymers, such as partially etherified cellulose derivatives, comprising carboxym ethyl-, hydroxyethyl-, hydroxypropyl-, hydroxypropylmethyl- or methylcellulose; completely synthetic hydrophilic polymers comprising polyacrylates, polymethacrylatcs, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide. (hydrazine cross-linked) hyaluronic acid, silicone; natural gums comprising alginates, carrageenan, guar-gum, gelatine, tragacanth, (amidated) pectin, xanthan, chitosan collagen, agarose; mixtures and further derivatives or copolymers thereof and/or other pharmaceutically, or at least biologically, acceptable polymers.

The formulations of the present invention may also comprise a polar liquid medium. The formulations of the invention may be administered in an aqueous medium. The of the present invention may be in the form of a solution, suspension, emulsion, cream, lotion, ointment, gel, spray, film forming solution or lacquer.

In some embodiments, the invention relates to the use of a vesicular formulation as described above for the preparation of a pharmaceutical composition for the treatment of disorders related to fatty acid deficiencies, fatty acid metabolism, hypertriglyceridemia and hypercholesterolemia. In some embodiments, the invention relates to a vesicular formulation or pharmaceutical composition comprising at least one phospholipid and one nonionic surfactant for the treatment of disorders related to fatty acid deficiencies, fatty acid metabolism, hypertriglyceridemia and hypercholesterolemia wherein the formulation or pharmaceutical composition is formulated for subcutaneous, topical or intravenous delivery.

While not to be limited to any mechanism of action or any theory, the formulations of the invention may form vesicles or ESAs characterized by their adaptability, deformability, or penetrability. Vesicles of this invention as described in both WO 2010/140061 and in WO 2011/022707.

EXAMPLES

Example 1

Example Formulations

The following exemplary formulations for topical application may be prepared by the following procedure:
1. Organic phase production, which contains all lipophilic excipients The organic phase is produced by weighing the lipid, the surfactant, any additional lipophilic excipients into suitable containers followed by mixing these components into anoptically isotropic phase which appears as a clear solution. During mixing, the organic phase will be heated up, but temperature must not rise above 45° C.
2. Aqueous phase production The aqueous phase is prepared by weighing the non-lipophilic components and water, which serves as solvent, into suitable containers and then mixing these components into a clear solution. During mixing, the temperature will be elevated to 40° C.
3. Production of a concentrated intermediate by combination of both phases The isotropic organic phase and the clear aqueous phase are combined under stirring in a suitable vessel. Before and during the combination the temperature of both phases must be kept between 35° C. and 45° C. The resulting intermediate is homogenised mechanically at 40° C. Before starting homogenisation, the pressure in the production vessel is lowered to −0.08 MPa. The desired average carrier size is typically reached after 10 minutes of homogenisation.

Three process parameters must be controlled carefully during the production of the concentrated intermediate: temperature, homogeniser circulation velocity, and overall processing time.

4. Production of the final bulk product by mixing the concentrated intermediate with dilution buffer.

The concentrated intermediate is diluted with the dilution buffer to the intended final concentration. The mixture is carefully stirred in the mixing vessel at 20° C. to homogeneity.

Table 8 describes the amounts of surfactant and lipids, and other excipients in the Deformasomes formulations, described in terms of the percent of the vesicular formulation.

Example Formulation 1

Formulation 1 comprises sphingomyelin (brain) (47.944 mg/g) as a lipid, Tween 80 (42.05 mg/g) as a surfactant, lactate buffer (pH 4). benzyl alcohol or paraben (5.000 mg/g) as an antimicrobial agent, BHT (0.200 mg/g) and sodium metabisulfite (0.0500 mg/g) as antioxidants, glycerol (30.000 mg/g), EDTA (3.000 mg/g) as a chelating agent, and ethanol (30.000 mg/g).

Example Formulation 2

Formulation 2 comprises sphingomyelin (brain) (53.750 mg/g) as a lipid, Tween 80 (31.250 mg/g) as a surfactant, lactate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (15.000 mg/g).

Example Formulation 3

Formulation 3 comprises sphingomyelin (brain) (90.561 mg/g) as a lipid, Tween 80 (79.439 mg/g) as a surfactant, lactate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 4

Formulation 4 comprises sphingomyelin (brain) (47.944 mg/g) as a lipid, Tween 80 (42.056 mg/g) as a surfactant, lactate (pH 5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 5

Formulation 5 comprises sphingomyelin lauroyl (50.607 mg/g) as a lipid, Brij 98 (44.393 mg/g) as a surfactant, acetate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 6

Formulation 6 comprises sphingomyelin lauroyl (90.561 mg/g) as a lipid, Brij 98 (79.439 mg/g) as a surfactant, acetate (pH 5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 7

Formulation 7 comprises sphingomyelin lauroyl (49.276 mg/g) as a lipid, Brij 98 (79.439 mg/g) as a surfactant, acetate (pH 6.5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 8

Formulation 8 comprises phosphatidyl choline and phosphatidyl glycerol (53.750 mg/g) as a lipid, Brij 98 (31.250 mg/g) as a surfactant, phosphate (pH 6.5) buffer, benzyl alcohol or paraben (5.000 mg/g) as an antimicrobial agent, HTHQ (0.200 mg/g) as an antioxidant, glycerol (30.000 mg/g), and EDTA (3.000 mg/g) as a chelating agent.

Example Formulation 9

Formulation 9 comprises phosphatidyl choline and phosphatidyl glycerol (90.561 mg/g) as a lipid, Brij 98 (79.439 mg/g) as a surfactant, phosphate (pH 6.5) buffer, benzyl alcohol or paraben (5.000 mg/g) as an antimicrobial agent, HTHQ (0.200 mg/g) as an antioxidant, glycerol (30.000 mg/g), EDT[Lambda] (3.000 mg/g) as a chelating agent, and ethanol (30.000 mg/g).

Example Formulation 10

Formulation 10 comprises phosphatidyl choline and phosphatidyl glycerol (41.351 mg/g) as a lipid. Brij 98 (48.649 mg/g) as a surfactant, phosphate (pH 4) buffer, benz>1 alcohol or paraben (5.000 mg/g) as an antimicrobial agent, HTIIQ (0.200 mg/g) as an antioxidant, glycerol (30.000 mg/g), EDTA (3.000 mg/g) as a chelating agent, and ethanol (30.000 mg/g).

Example Formulation 11

Formulation 1 1 comprises phosphatidyl choline and phosphatidyl glycerol (47.882 mg/g) as a lipid. Brij 98 (37.1 18 mg/g) as a surfactant, phosphate (pH 4) buffer, benzyl alcohol or paraben (5.000 mg/g) as an antimicrobial agent, HTHQ (0.200 mg/g) as an antioxidant, glycerol, EUTA (3,000 mg/g) as a chelating agent, and ethanol (30.000 mg/g).

Example Formulation 12

Formulation 12 comprises phosphatidyl choline and phosphatidyl glycerol (95.764 mg/g) as a lipid, Brij 98 (74.236 mg/g) as a surfactant, phosphate (pI 4) buffer, benzyl alcohol or paraben (5.000 mg/g) as an antimicrobial agent, HTHQ (0.200 mg/g) as an antioxidant, glycerol (30.000 mg/g), EDTA (3.000 mg/g) as a chelating agent, and ethanol (30.000 mg/g).

Example Formulation 13

Formulation 13 comprises phosphatidyl choline and phosphatidylinositol (66.676 mg/g) as a lipid, Span 20 (24.324 mg/g) as a surfactant, acetate (pH 5) buffer, benzyl alcohol or paraben (5.000 mg/g), 1 ITI IQ (0.200 mg/g) as an antioxidant, EDTA (3.000 mg/g) as a chelating agent, and ethanol (25.000 mg/g).

Example Formulation 14

Formulation 14 comprises phosphatidyl choline and phosphatidylinositol (62.027 mg/g) as a lipid, Span 20 (22.973 mg/g) as a surfactant, acetate (pH 5) buffer, benzyl alcohol or paraben (5.000 mg/g) as an antimicrobial agent, HTHQ (0.200 mg/g) as an antioxidant, EDTA (3.000 mg/g) as a chelating agent, and ethanol (30.000 mg/g).

Example Formulation 15

Formulation 15 comprises phosphatidyl choline and phosphatidylinositol (124.054 mg/g) as a lipid, Span 20 (45.946 mg/g) as a surfactant, acetate (pH 5) buffer, benzyl alcohol or paraben (5.000 mg/g) as an antimicrobial agent, HTHQ (0.200 mg/g) as an antioxidant, glycerol (30.000 mg/g), and EDTA (3.000 mg/g) as a chelating agent, and ethanol (36.510 mg/g).

Example Formulation 16

Formulation 16 comprises phosphatidyl choline and phosphatidylinositol (62.687 mg/g) as a lipid, Span 20 (32,313 mg/g) as a surfactant, acetate (pH 6.5) buffer, benzyl alcohol or paraben (5.000 mg/g) as an antimicrobial agent, HTHQ (0.200 mg/g) as an antioxidant, glycerol (30.000 mg/g), EDTA (3.000 mg/g) as a chelating agent.

Example Formulation 17

Formulation 17 comprises phosphatidyl choline and phosphatidic acid (41.853 mg/g) as a lipid, Tween 80 (43.147 mg/g) as a surfactant, phosphate (pH 6.5) buffer, benzyl alcohol or paraben (5.000 mg/g) as an antimicrobial agent, BHT (0.200 mg/g) as an antioxidant, glycerol (30.000 mg/g), EDTA (3.000 mg/g), and ethanol (30.000 mg/g).

Example Formulation 18

Formulation 18 comprises phosphatidyl choline and phosphatidic acid (95.764 mg/g) as a lipid, Tween 80 (74.236 mg/g) as a surfactant, phosphate (pH 6.5) buffer, benzyl alcohol or paraben (5.000 mg/g) as an antimicrobial agent, BHT (0.200 mg/g) as an antioxidant, EDTA (3.000 mg/g), and ethanol (30.000 mg/g).

Example Formulation 19

Formulation 19 comprises phosphatidyl choline and phosphatidic acid (47.882 mg/g) as a lipid, Brij 98 and Tween 80 (37.118 mg/g) as a surfactant, phosphate (pH 6.5) buffer, benzyl alcohol or paraben (5.000 mg/g) as an antimicrobial agent, BHT (0.200 mg/g) as an antioxidant, and EDTA (3.000 mg/g).

Example Formulation 20

Formulation 20 comprises phosphatidyl choline and phosphatidic acid (45.000 mg/g) as a lipid, Span 20 and Tween 80 (45.000 mg/g) as a surfactant, phosphate (pH 6.5) buffer, benzyl alcohol or paraben (5.000 mg/g) as an antimicrobial agent, BHT (0.200 mg/g) as an antioxidant, and EDTA (1.000 mg/g).

Example Formulation 21

Formulation 21 comprises phosphatidyl choline (31.935 mg/g) as a lipid, cremophor and Span 20 (58.065 mg/g) as a surfactant, lactate (pH 5) buffer, thimerosal (5.000 mg/g) as an antimicrobial agent, BHA (0,200 mg/g) as an antioxidant, glycerol (30.000 mg/g), EDTA (3.000 mg/g) as a chelating agent, and ethanol (15.000 mg/g).

Example Formulation 22

Formulation 22 comprises phosphatidyl choline (42.500 mg/g) as a lipid, cremophor and Tween 80 (42.500 mg/g) as a surfactant, lactate (pH 6,5) buffer, thimerosal (5.000 mg/g) as an antimicrobial agent, BHA (0.200 mg/g) as an antioxidant, glycerol (30.000 mg/g). and EDTA (3.000 mg/g) as a chelating agent.

Example Formulation 23

Formulation 23 comprises phosphatidyl choline (38.276 mg/g) as a lipid, cremophor (51.724 mg/g) as a surfactant, lactate (pH 4) buffer, thimerosal (5.000 mg/g) as an antimicrobial agent. BHA (0.200 mg/g) as an antioxidant, EDTA (3.000 mg/g) as a chelating agent, and ethanol (36.510 mg/g).

Example Formulation 24

Formulation 24 comprises phosphatidyl choline (42.500 mg/g) as a lipid, cremophor (42.500 mg/g) as a surfactant, lactate (pH 4) buffer, thimerosal (5.000 mg/g) as an antimicrobial agent, BHA (0.200 mg/g) as an antioxidant, EDTA (3.000 mg/g) as a chelating agent, and ethanol (15.000 mg/g).

Example Formulation 25

Formulation 25 comprises phosphatidyl choline (85.000 mg/g) as a lipid, cremophor (85.000 mg/g) as a surfactant, lactate (pH 4) buffer, thimerosal (5.000 mg/g) as an antimicrobial agent, BHA (0.200 mg/g) as an antioxidant, EDTA (3.000 mg/g) as a chelating agent, and ethanol (30.000 mg/g).

Example Formulation 26

Formulation 26 comprises phosphatidyl choline (38.276 mg/g) as a lipid, cremophor (51.276 mg/g) as a surfactant, lactate (pH 5) buffer, thimerosal (5.000 mg/g) as an antimicrobial agent, BHA (0.200 mg/g) as an antioxidant, and EDTA (1.000 mg/g) as a chelating agent.

Example Formulation 27

Formulation 27 comprises phosphatidyl choline (36.429 mg/g) as a lipid, cremophor (48.571 mg/g) as a surfactant, lactate (pH 5) buffer, thimerosal (5.000 mg/g) as an antimicrobial agent, BHA (0.200 mg/g) as an antioxidant, EDTA (3.000 mg/g) as a chelating agent, and ethanol (30.000 mg/g).

Example Formulation 28

Formulation 28 comprises phosphatidyl choline (72.299 mg/g) as a lipid, cremophor (97,701 mg/g) as a surfactant, lactate (pH 5) buffer, thimerosal (5.000 mg/g) as an antimicrobial agent, BHA (0.200 mg/g) as an antioxidant, EDTA (3.000 mg/g) as a chelating agent, and ethanol (15.000 mg/g).

Example Formulation 29

Formulation 29 comprises phosphatidyl ethanolamine (46.250 mg/g) as a lipid, Tween 80 (46.250 mg/g) as a surfactant, phosphate (pH 6.5) buffer, thimerosal (5.000 mg/g) as an antimicrobial agent, BHT (0.200 mg/g) and sodium metabisulfite (0.500 mg/g) as an antioxidant, EDTA (3.000 mg/g) as a chelating agent, and ethanol (20.000 mg/g).

Example Formulation 30

Formulation 30 comprises phosphatidyl ethanolamine (38.804 mg/g) as a lipid, Tween 80 (46.196 mg/g) as a surfactant, phosphate (pH 6.5) buffer, thimerosal (5.000 mg/g) as an antimicrobial agent, BHT (0.200 mg/g) and sodium metabisulfite (0.500 mg/g) as an antioxidant, glycerol (15.000 mg/g), EDTA (3.000 mg/g) as a chelating agent, and ethanol (30.000 mg/g).

Example Formulation 31

Formulation 31 comprises phosphatidyl ethanolamine (36.667 mg/g) as a lipid, Brij 98 and Tween 80 (33.333 mg/g) as a surfactant, phosphate (pH 6.5) buffer, thimerosal (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 32

Formulation 32 comprises phosphatidyl glycerol (23.333 mg/g) as a lipid, cremophor and Brij 98 (66.667 mg/g) as a surfactant, acetate (pH 4) buffer, benzyl alcohol or paraben (5.000 mg/g) as an antimicrobial agent, BHT (0.200 mg/g) as an antioxidant, and EDTA (3.000 mg/g) as a chelating agent.

Example Formulation 33

Formulation 33 comprises phosphatidyl glycerol (45.833 mg/g) as a lipid, Brij 98 (41.667 mg/g) as a surfactant, acetate (pH 4) buffer, benzyl alcohol or paraben (5.000 mg/g) as an antimicrobial agent, BHT (0.200 mg/g) as an antioxidant, glycerol (30.000 mg/g), and EDTA (3.000 mg/g) as a chelating agent.
Formulation 34 comprises phosphatidyl glycerol (31.957 mg/g) as a lipid, Brij 98 (38.043 mg/g) as a surfactant, acetate (pH 4) buffer, benzyl alcohol or paraben (5.000 mg/g) as an antimicrobial agent. BHT (0.200 mg/g) as an antioxidant, EDTA (3.000 mg/g) as a chelating agent, and ethanol (30.000 mg/g).

Example Formulation 35

Formulation 35 comprises phosphatidyl glycerol (47.143 mg/g) as a lipid, Brij 98 (42.857 mg/g) as a surfactant, acetate (pH 5) buffer, benzyl alcohol or paraben (5.000 mg/g) as an antimicrobial agent, BHT (0.200 mg/g) as an antioxidant, glycerol (30.000 mg/g), EDT[Lambda] (1.000 mg/g) as a chelating agent, and ethanol (25.000 mg/g).

Example Formulation 36

Formulation 36 comprises phosphatidyl glycerol (96.905 mg/g) as a lipid, Brij 98 (88.095 mg/g) as a surfactant, acetate (pH 5) buffer, benzyl alcohol or paraben (5.000 mg/g) as an antimicrobial agent, BHT (0.200 mg/g) as an antioxidant, glycerol (30.000 mg/g), EDTA (3.000 mg/g) as a chelating agent, and ethanol (20.000 mg/g).

Example Formulation 37

Formulation 37 comprises phosphatidyl glycerol (31.957 mg/g) as a lipid, Brij 98 (38.043 mg/g) as a surfactant, acetate (pH 5) buffer, benzyl alcohol or paraben (5.000 mg/g) as an antimicrobial agent, BHT (0.200 mg/g) as an antioxidant, EDTA (3.000 mg/g) as a chelating agent, and ethanol (30.000 mg/g).

Example Formulation 38

Formulation 38 comprises phosphatidyl ethanolamine (35.455 mg/g) as a lipid, cremophor (54.545 mg/g) as a surfactant, phosphate (pH 6.5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 39

Formulation 39 comprises phosphatidyl ethanolamine (84.457 mg/g) as a lipid, cremophor (100.543 mg/g) as a surfactant, phosphate (pH 6.5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 40

Formulation 40 comprises phosphatidyl ethanolamine (89.048 mg/g) as a lipid, cremophor (80.952 mg/g) as a surfactant, phosphate (pH 6.5) buffer, benzyl alcohol or paraben (5.000 mg/g), BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 41

Formulation 41 comprises phosphatidyl glycerol (41.087 mg/g) as a lipid, Tween 80 (48.913 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (36.510 mg/g).

Example Formulation 42

Formulation 42 comprises phosphatidyl glycerol (45.280 mg/g) as a lipid, Tween 80 (39.720 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g), and EDTA (3.000 mg/g) as a chelating agent.

Example Formulation 43

Formulation 43 comprises phosphatidyl glycerol (107.500 mg/g) as a lipid, Tween 80 (62.500 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 44

Formulation 44 comprises phosphatidyl glycerol (77.243 mg/g) as a lipid, Tween 80 (67.757 mg/g) as a surfactant, propionate (pH 4) buffer, benzyl alcohol or paraben (5.000 mg/g) as an antimicrobial agent. BHT (0.200 mg/g) and sodium metabisulfite (0.500 mg/g) as antioxidants. EDTA (3,000 mg/g) as a chelating agent, and ethanol (30.000 mg/g).

Example Formulation 45

Formulation 45 comprises phosphatidyl glycerol (45.280 mg/g) as a lipid, Tween 80 (39.720 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 46

Formulation 46 comprises phosphatidyl glycerol (90.561 mg/g) as a lipid, Tween 80 (79.439 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 47

Formulation 47 comprises phosphatidyl glycerol (47.944 mg/g) as a lipid, Tween 80 (42.056 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 48

Formulation 48 comprises phosphatidyl serine (50.607 mg/g) as a lipid, Brij 98 (44.393 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), and EDTA (1.000 mg/g) as a chelating agent.

Example Formulation 49

Formulation 49 comprises phosphatidyl serine (107.500 mg/g) as a lipid, Brij 98 (62.500 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), and ED1 A (3.000 mg/g) as a chelating agent.

Example Formulation 50

Formulation 50 comprises phosphatidyl serine (47.944 mg/g) as a lipid, Brij 98 (42.056 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 51

Formulation 51 comprises phosphatidyl glycerol (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (25.000 mg/g).

Example Formulation 52

Formulation 52 comprises phosphatidyl glycerol (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, EDTA (3.000 mg/g) as a chelating agent, and ethanol (20.000 mg/g).

Example Formulation 53

Formulation 53 comprises phosphatidyl glycerol (46.098 mg/g) as a lipid, Brij 98 (43.902 mg/g) as a surfactant, acetate (pH 5) buffer, benzyl alcohol or paraben (5.000 mg/g) as an antimicrobial, BHT (0.200 mg/g) as an antioxidant, glycerol (15.000 mg/g), EDTA (3.000 mg/g) as a chelating agent, and ethanol (30.000 mg/g).

Example Formulation 54

Formulation 54 comprises phosphatidyl glycerol (43.537 mg/g) as a lipid, Brij 98 (41.463 mg/g) as a surfactant, acetate (pH 5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 55

Formulation 55 comprises phosphatidyl glycerol (45.000 mg/g) as a lipid, Brij 98 (45.000 mg/g) as a surfactant, acetate (pH 5) buffer, benzyl alcohol or paraben (5.000 mg/g) as an antimicrobial, BHT (0.200 mg/g) as an antioxidant, EDTA (3.000 mg/g) as a chelating agent, and ethanol (30.000 mg/g).

Example Formulation 56

Formulation 56 comprises phosphatidyl glycerol (59.492 mg/g) as a lipid, Brij 98 (30.508 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (30.000 mg/g).

Example Formulation 57

Formulation 57 comprises phosphatidyl glycerol (39.054 mg/g) as a lipid, Brij 98 (45.946 mg/g) as a surfactant, acetate (pH 6.5) buffer, benzyl alcohol or paraben (5.000 mg/g) as an antimicrobial, BHT (0.200 mg/g) as an antioxidant, and EDTA (3.000 mg/g) as a chelating agent.

Example Formulation 58

Formulation 58 comprises phosphatidyl glycerol (35.854 mg/g) as a lipid, Brij 98 (34.146 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 59

Formulation 59 comprises phosphatidyl choline (50.000 mg/g) as a lipid, Tween 80 (40.000 mg/g) as a surfactant, phosphate (pH 6.5) buffer, benzyl alcohol or paraben (5.000 mg/g) as an antimicrobial, BHT (0.200 mg/g) and sodium metabisulf[iota]te (0.500 mg/g) as antioxidants, glycerol (30.000 mg/g), EDTA (3.000 mg/g) as a chelating agent, and ethanol (30.000 mg/g).

Example Formulation 60

Formulation 60 comprises phosphatidyl choline (38.571 mg/g) as a lipid, Tween 80 (51.429 mg/g) as a surfactant phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 61

Formulation 61 comprises phosphatidyl choline (41.954 mg/g) as phospholipid, Tween 80 (50.546 mg/g) as surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 62

Formulation 62 comprises phosphatidyl choline (42.632 mg/g) as a lipid, Tween 80 (47.368 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 63

Formulation 63 comprises phosphatidyl choline (46.098 mg/g) as a lipid, Tween 80 (43.902 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 64

Formulation 64 comprises phosphatidyl choline (39.721 mg/g) as a lipid, Tween 80 (50.279 mg/g) as a surfactant, phosphate (pH 6.5) buffer, benzyl alcohol or paraben (5.000 mg/g) as an antimicrobial, BH T (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 65

Formulation 65 comprises phosphatidyl choline (44.198 mg/g) as a lipid, Tween 80 (50.802 mg/g) as a surfactant, phosphate (pH 6.5) buffer, benzyl alcohol or paraben (5.000 mg/g) as an antimicrobial, BHT (0,200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 66

Formulation 66 comprises phosphatidyl choline (46.453 mg/g) as a lipid, Tween 80 (51.047 mg/g) as a surfactant, phosphate (pH 6.5) buffer, benzyl alcohol or paraben (5.000 mg/g) as an antimicrobial. BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Formulation 67 comprises phosphatidyl choline (51.221 mg/g) as a lipid, Tween 80 (43.779 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 68

Formulation 68 comprises phosphatidyl choline (54.167 mg/g) as a lipid, Tween 80 (43.333 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 69

Formulation 69 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 69 is an emulsion.

Example Formulation 70

Formulation 70 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 70 is a suspension.

Example Formulation 71

Formulation 71 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0,500 mg/g) as antioxidants, glycerol (30.000 mg/g), EDTA (3.000 mg/g) as a chelating agent, and ethanol (30.000 mg/g).

Formulation 72 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 72 is an emulsion.

Example Formulation 73

Formulation 73 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 73 is a suspension.

Example Formulation 74

Formulation 74 comprises phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 75

Formulation 75 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 76

Formulation 76 comprises phosphatidyl choline (40.000 mg/g) as a lipid, Brij 98 (50.000 mg/g) as a surfactant, phosphate (pH 6.5) buffer, benzalkonium chloride (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 77

Formulation 77 comprises phosphatidyl choline (40.000 mg/g) as a lipid, Tween 80 (50.000 mg/g) as a surfactant, phosphate (pH 6.5) buffer, benzyl alcohol or paraben (5,000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 78

Formulation 78 comprises phosphatidyl choline (66.440 mg/g) as a lipid, Brij 98 (23.560 mg/g) as a surfactant, phosphate (pH 6.5) buffer, benzalkonium chloride (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 79

Formulation 79 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 80

Formulation 80 comprises phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 81

Formulation 81 comprises phosphatidyl choline (40.000 mg/g) as a lipid, Tween 80 (50.000 mg/g) as a surfactant, acetate (pH 5.5) buffer, benzyl alcohol or paraben (5.000 mg/g) as an antimicrobial. BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 82

Formulation 82 comprises phosphatidyl choline (44.444 mg/g) as a lipid, Tween 80 (55.556 mg/g) as a surfactant, acetate (pH 5.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 83

Formulation 83 comprises phosphatidyl choline (66.440 mg/g) as a lipid, Tween 80 (23.560 mg/g) as a surfactant, acetate (pH 5.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 84

Formulation 84 comprises phosphatidyl choline (54.000 mg/g) as a lipid, Tween 80 (36.000 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 85

Formulation 85 comprises phosphatidyl choline (50.000 mg/g) as a lipid, Tween 80 (40.000 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g)

Example Formulation 86

Formulation K6 comprises phosphatidyl choline (48.611 mg/g) as a lipid. Tween 80 (38.889 mg/g) as a surfactant, acetate (pH 4) buffer, benzyl alcohol or paraben (5.000 mg/g) as an antimicrobial, BH[Lambda] (0.200 mg/g) and sodium metabisulfite (0,500 mg/g) as antioxidants, glycerol (30.000 mg/g), EDTA (3.000 mg/g) as a chelating agent, and ethanol (30.000 mg/g).

Example Formulation 87

Formulation 87 comprises phosphatidyl choline (46.575 mg/g) as a lipid, Tween 80 (38,425 mg/g) as a surfactant, acetate (pH 4) buffer, benzyl alcohol or paraben (5.000 mg/g) as an antimicrobial, BHA (0.200 mg/g) and sodium metabisulf[iota]te (0.500 mg/g) as antioxidants, glycerol (30,000 mg/g), EDTA (3.000 mg/g) as a chelating agent, and ethanol (30.000 mg/g). Example formulation 87 is an emulsion.

Example Formulation 88

Formulation 88 comprises phosphatidyl choline (46.575 mg/g) as a lipid, Tween 80 (38.425 mg/g) as a surfactant, acetate (pH 4) buffer, benzyl alcohol or paraben (5.000 mg/g) as an antimicrobial, BHA (0.200 mg/g) and sodium metabisulf[iota]te (0.500 mg/g) as antioxidants, glycerol (30.000 mg/g), EDTA (3.000 mg/g) as a chelating agent, and ethanol (30.000 mg/g). Example formulation 88 is suspension.

Example Formulation 89

Formulation 89 comprises phosphatidyl choline (46.575 mg/g) as a lipid, Tween 80 (38.425 mg/g) as a surfactant, acetate (pH 4) buffer, benzyl alcohol or paraben (5.000 mg/g) as an antimicrobial, BUT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 90

Formulation 90 comprises phosphatidyl choline (50.000 mg/g) as a lipid, Tween 80 (40.000 mg/g) as a surfactant, acetate (pH 4.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 91

Formulation 91 comprises phosphatidyl choline (94.444 mg/g) as a lipid, Tween 80 (75.556 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 92

Formulation 92 comprises phosphatidyl choline (46.712 mg/g) as a lipid, Tween 80 (38.288 mg/g) as a surfactant, acetate (pH 4) buffer, benzyl alcohol or paraben (5.000 mg/g) as an antimicrobial. BHT (0.200 mg/g) and sodium metabisulfite (0.500 mg/g) as antioxidants, glycerol (30.000 mg/g). EDTA (3.000 mg/g) as a chelating agent, and ethanol (30.000 mg/g).

Example Formulation 93

Formulation 93 comprises phosphatidyl choline (48.889 mg/g) as a lipid, Tween 80 (39.111 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 94

Formulation 94 comprises phosphatidyl choline (39.721 mg/g) as a lipid, Tween 80 (50.279 mg/g) as a surfactant, phosphate (pH 6.5) buffer, benzyl alcohol or paraben (5.25 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 95

Formulation 95 comprises phosphatidyl choline (90.000 mg/g) as a lipid, phosphate buffer (pH 6.5), benzyl alcohol or paraben as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 96

Formulation 96 comprises phosphatidyl choline (68.700 mg/g) as a lipid, Tween 80 (8.500 mg/g) as a surfactant, phosphate (pH 7.5) buffer, BHT (0.200 mg/g) and sodium metabisulfite (0.500 mg/g) as antioxidants, benzyl alcohol or paraben (5.000 mg/g) as an antimicrobial, glycerol (30.000 mg/g), EDTA (1.000 mg/g) as a chelating agent, and ethanol (36.51 mg/g).

Example Formulation 97

Formulation 97 comprises phosphatidyl choline (71.460 mg/g) as a lipid, Tween 80 (4.720 mg/g) as a surfactant, phosphate (pH 7.5) buffer. BHA (0.200 mg/g) and sodium metabisulfite (0.500 mg/g) as antioxidants, benzyl alcohol or paraben (5.000 mg/g) as an antimicrobial, glycerol (50.000 mg/g), EDTA (3.000 mg/g) as a chelating agent and ethanol (35.000 mg/g).

Example Formulation 98

Formulation 98 comprises phosphatidyl choline (71.460 mg/g) as a lipid, Tween 80 (4.720 mg/g) as a surfactant, phosphate (pH 7.8) buffer. BHA (0.200 mg/g) and sodium metabisulfite (0.500 mg/g) as antioxidants, benzyl alcohol or paraben (5.000 mg/g) as an antimicrobial, glycerol (15.000 mg/g), EDTA (3.000 mg/g) as a chelating agent, and ethanol (35.000 mg/g).

Example Formulation 99

Formulation 99 comprises phosphatidyl choline (71.460 mg/g) as a lipid, Tween 80 (4.720 mg/g) as a surfactant, phosphate (pH 7.8) buffer, BHA (0.200 mg/g) and sodium metabisulfite (0.500 mg/g) as antioxidants, glycerol (50.000 mg/g), EDTA (3.000 mg/g) as a chelating agent, and ethanol (15.000 mg/g).

Example Formulation 100

Formulation 100 comprises phosphatidyl choline (71.4600 mg/g) as a lipid, Tween 80 (4.720 mg/g) as a surfactant, phosphate (pH 7.5) buffer, BHA (0.200 mg/g) and sodium metabisulfite (0.500 mg/g) as antioxidants, glycerol (50.000 mg/g), EDTA (3.000 mg/g) as a chelating agent, and ethanol (35.000 mg/g).

Example Formulation 101

Formulation 101 comprises phosphatidyl choline (46.575 mg/g) as a lipid, Tween 80 (38.425 mg/g) as a surfactant, phosphate (pI I 4) buffer, BHT (0.500 mg/g) and sodium metabisulfite (0.200 mg/g) as antioxidants, and EDTA (3.000 mg/g) as a chelating agent. Example formulation 101 is an emulsion.

Example Formulation 102

Formulation 102 comprises phosphatidyl choline (46.575 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g). Example formulation 102 is a suspension.

Example Formulation 103

Formulation 103 comprises phosphatidyl choline (54.643 mg/g) as a lipid, Tween 80 (30.357 mg/g) as a surfactant, phosphate (pH 4) buffer, BHA (0.500 mg/g) and sodium metabisulfite (0.200 mg/g) as antioxidants, and EDTA (3.000 mg/g) as a chelating agent.

Example Formulation 104

Formulation 104 comprises phosphatidyl choline (39.72 mg/g) as a lipid, Tween 80 (50.279 mg/g) as surfactant, phosphate (pH 6.5) buffer, benzyl alcohol or paraben (5.00 mg/g) as an antimicrobial, BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 105

Formulation 105 comprises phosphatidyl choline (90.00 mg/g) as a lipid, phosphate (pH 6.5) buffer, benzyl alcohol or paraben as antimicrobial (5.000 mg/s), BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 106

Formulation 106 comprises phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 106 is formulated as an emulsion.

Example Formulation 107

Formulation 107 comprises phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 107 as a suspension.

Example Formulation 108

Formulation 108 comprises phosphatidyl choline (54.64 mg/g) as a lipid, Tween 80 (30.357 mg/g) as a surfactant, phosphate (pH 4) buffer, BHA (0.500 mg/g) and sodium metabisulfite (0.200 mg/g) as antioxidants, EDTA (3.000 mg/g) as the chelating agent.

Example Formulation 109

Formulation 109 comprises phosphatidyl glycerol and lysophospholipid (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (25.000 mg/g).

Example Formulation 110

Formulation 110 comprises phosphatidyl glycerol and lysophospholipid (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, EDTA (3.000 mg/g) as a chelating agent, and ethanol (20.000 mg/g).

Example Formulation 111

Formulation 111 comprises phosphatidyl glycerol and lysophospholipid (46.098 mg/g) as a lipid, Brij 98 (43.902 mg/g) as a surfactant, acetate (pH 5) buffer, benzyl alcohol or paraben (5.000 mg/g) as an antimicrobial, BHT (0.200 mg/g) as an antioxidant, glycerol (15.000 mg/g), EDTA (3.000 mg/g) as a chelating agent, and ethanol (30.000 mg/g).

Example Formulation 112

Formulation 1 12 comprises phosphatidyl glycerol and lysophospholipid (43.537 mg/g) as a lipid, Brij 98 (41.463 mg/g) as a surfactant, acetate (pH 5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 113

Formulation 113 comprises phosphatidyl glycerol and lysophospholipid (45.000 mg/g) as a lipid, Brij 98 (45.000 mg/g) as a surfactant, acetate (pH 5) buffer, benzyl alcohol or paraben (5.000 mg/g) as an antimicrobial, BHT (0.200 mg/g) as an antioxidant, EDTA (3.000 mg/g) as a chelating agent, and ethanol (30,000 mg/g).

Example Formulation 114

Formulation 114 comprises phosphatidyl glycerol and lysophospholipid (59.492 mg/g) as a lipid, Brij 98 (30.508 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (30.000 mg/g).

Example Formulation 115

Formulation 1 15 comprises phosphatidyl glycerol and lysophospholipid (39.054 mg/g) as a lipid, Brij 98 (45,946 mg/g) as a surfactant, acetate (pH 6.5) buffer, benzyl alcohol or paraben (5.000 mg/g) as an antimicrobial, BHT (0.200 mg/g) as an antioxidant, and EDTA (3.000 mg/g) as a chelating agent.

Example Formulation 116

Formulation 116 comprises phosphatidyl glycerol and lysophospholipid (35.854 mg/g) as a lipid, Brij 98 (34.146 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 117

Formulation 117 comprises phosphatidyl choline and lysophospholipid (50.000 mg/g) as a lipid, Tween 80 (40.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 118

Formulation 118 comprises phosphatidyl choline and lysophospholipid (38.571 mg/g) as a lipid, Tween 80 (51.429 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 119

Formulation 119 comprises phosphatidyl choline and lysophospholipid (41.954 mg/g) as phospholipid, Tween 80 (50.546 mg/g) as surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 120

Formulation 120 comprises phosphatidyl choline and lysophospholipid (42.632 mg/g) as a lipid, Tween 80 (47.368 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 121

Formulation 121 comprises phosphatidyl choline and lysophospholipid (46.098 mg/g) as a lipid, Tween 80 (43.902 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 122

Formulation 122 comprises phosphatidyl choline and lysophospholipid (39.721 mg/g) as a lipid, Twecn 80 (50.279 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 123

Formulation 123 comprises phosphatidyl choline and lysophospholipid (44.198 mg/g) as a lipid, Tween 80 (50.802 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 124

Formulation 124 comprises phosphatidyl choline and lysophospholipid (46.453 mg/g) as a lipid, Tween 80 (51.047 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 125

Formulation 125 comprises phosphatidyl choline and lysophospholipid (51.221 mg/g) as a lipid. Tween 80 (43.779 mg/g) as a surfactant, phosphate (pH 6.5) buffer, benzyl alcohol or paraben (5.000 mg/g) as an antimicrobial, BHT (0.200 mg/g) and sodium mctabisulfite (0.500 mg/g) as antioxidants, glycerol (30.000 mg/g), EDTA (3.000 mg/g) as a chelating agent, and ethanol (30.000 mg/g).

Example Formulation 126

Formulation 126 comprises phosphatidyl choline (54.167 mg/g) as a lipid, Twcen 80 (43.333 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 127

Formulation 127 comprises phosphatidyl choline and lysophospholipid (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g) Example formulation 69 is an emulsion.

Example Formulation 128

Formulation 128 comprises phosphatidyl choline and lysophospholipid (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 70 is a suspension.

Example Formulation 129

Formulation 129 comprises phosphatidyl choline and lysophospholipid (66.440 mg/g) as a lipid. Brij 98 (23.560 mg/g) as a surfactant, phosphate (pH 6.5) buffer, benzyl alcohol or paraben (5.000 mg/g) as an antimicr[upsilon]bial. BHT (0 200 mg/g) and sodium metabisulfite (0.500 mg/g) as antioxidants, glycerol (30.000 mg/g), EDTA (3.000 mg/g) as a chelating agent, and ethanol (30.000 mg/g).

It will be understood that the exact amounts of the components of the formula may be adjusted slightly without departing from the scope of the invention. For example, in each of the above formulations, the amount antimicrobial be anywhere from about 1 mg/g to about 15 mg/g, or about 5 m/g to about 12 mg/g, or 5.25 mg/g, 6, mg/6, 7 mg/g, 8 mg/g, 9 mg/g, 10 mg/g, or 10.25 mg/g. Furthermore, the antimicrobial can be a combination of ingredients, for example benzyl alcohol and parabenes (e.g., ethyl and/or propyl).

Example Formulations 1 through 129 may also optionally include thickeners such as pectin, xanthan gum. HPMC gel, methylcellulose or carbopol.

Example 2

A randomised, double-blind study of 4 weeks treatment duration in male or female subjects >18 and <85 years was carried out with clinically diagnosed rosacea subtype 1 (erythematotelangiectatic) defined by a score of 6-15 (inclusive) out of a maximum score of 30 for the primary and secondary features of the Rosacea Standard Grading System (RSGS). The subtype had to be defined using the global physicians rating by subtype of the RSGS.

The study consisted of a Screening visit, Baseline visit (Week 0), a telephone call at Week 1, visits at Week 2 and 4, and a follow-up telephone call at Week 5. Eligible subjects may or may not have been using medication for their rosacea at the time of screening. Subjects with concomitant use of rosacea treatments were taken off their current medication and returned for a Baseline Visit at the end of the wash-out period.

Eligible subjects were stratified by gender at a ratio of 4:1 (Female: Male) to account for the higher incidence of the disease in the female population. Within the strata, subjects were randomised at Baseline in a 2:1 ratio in favour of Formulation A to receive either "Formulation A" or vehicle.

"Formulation A" consisted of the following:

| Trade Name | Concentration [mg/g] |
| --- | --- |
| Phosphatidylcholine | 64.516 |
| Polysorbate 80 | 35.484 |
| Alcohol | 30.000 |
| Glycerol | 30.000 |
| Tromethamine | 12.677 |
| Carbomer | 10.000 |
| Disodium phosphate | 7.720 |
| Benzyl alcohol | 5.250 |
| Sodium phosphate | 4.440 |
| Disodium EDTA | 3.000 |
| Methylparaben | 2.500 |
| Ethylparaben | 1.700 |
| Linalool | 1.000 |
| BHA | 0.200 |
| Aqua | 791.513 |
| Total | 1000.000 |

Efficacy was evaluated using subject rating of the Rosacea Quality Of Life instrument (R-QOL) during office visits and applied over the phone during the week 1 and follow-up telephone call at Week 5. An investigator rating was performed using a "0=absent" to "3=severe" grading of the RSGS primary features flushing, non-transient erythema, papules and pustules, telangiectasia and the secondary features burning or stinging, plaques, dry appearance, edema, ocular manifestations and phymatous changes during the office visits. Ocular manifestations and phymatous changes needed to be absent to be eligible for the study.

Photographs to document treatment effects were taken at screening, baseline, week 2 and week 4.

Safety was monitored at each visit asking and examining patients for adverse events.

Results are shown in table 4, below:

TABLE 4

| Endpoint | Clinical Observation | Conclusion |
| --- | --- | --- |
| Non-transient erythema | Formulation A is statistically significantly better than vehicle (p = 0.044) after 4 weeks treatment for non-transient erythema according to the Investigator assessment (RSGS 2) | Formulation A is significantly better than placebo in reducing the underlying redness of rosacea |
| | Formulation A is statistically significantly better than vehicle (p = 0.039) after 4 weeks treatment in achieving at least one grade improvement for non-transient erythema according to the Investigator assessment (RSGS 2) | Formulation A is significantly better than placebo in achieving at least a 25% reduction in the underlying redness of rosacea |

TABLE 4-continued

| Endpoint | Clinical Observation | Conclusion |
| --- | --- | --- |
| | 39.5% of patients treated with Formulation A for 4 weeks show at least one grade improvement for non-transient erythema according to the Investigator assessment (RSGS 2) | 40% of patients treated with Formulation A show at least a 25% reduction in the underlying redness of their rosacea |
| | Patients treated with Formulation A show a highly statistically significant improvement for non-transient erythema after 2 weeks treatment (p = <0.0005) which is maintained after 4 weeks treatment (p = <0.0037) according to the Investigator assessment (RSGS 2) | Patients treated with Formulation A demonstrate a highly significant and sustained reduction in the underlying redness of their rosacea |
| Flushing | 50% of patients treated with Formulation A for 4 weeks show at least one grade improvement for flushing (transient erythema) according to the Investigator assessment (RSGS 1) | 50% of patients treated with Formulation A show at least a 25% reduction in flushing |
| | Patients treated with Formulation A show a highly statistically significant improvement for flushing (transient erythema) after 2 weeks treatment (p = <0.001) which is maintained after 4 weeks treatment (p = <0.001) according to the Investigator assessment (RSGS 1) | Patients treated with Formulation A demonstrate a highly significant and sustained reduction in their flushing |
| Teleangiectasia | 21.1% of patients treated with Formulation A for 4 weeks show at least one grade improvement for teleangiectasia according to the Investigator assessment (RSGS 4) | 21% of patients treated with Formulation A show at least a 25% reduction in the appearance of their thread veins |
| | Patients treated with Formulation A show a highly statistically significant improvement for teleangiectasia after 4 weeks treatment (p = <0.0078) according to the Investigator assessment (RSGS 4) | Patients treated with Formulation A demonstrate a highly significant reduction in the appearance of their thread veins |

Example 3

A 51 year old woman who had suffered with facial Rosacea and associated acne for more than 8 years had tried many and varied remedies including prescribed antibiotic medicine (tetracycline). The woman had also been to a private skin specialist who explained that there was little or no proven medicine for the treatment of Rosacea. The subject tried to manage the condition with very limited success but had to resort on a daily basis to coverage of the skin with cosmetics. The subject applied formulation X in a thin film over the affected areas and within half a day there was evidence of success. The flushing was seen to have diminished noticeably. Over the next two weeks the subject applied the formulation twice a day to the affected area. The condition was relieved entirely including an absence of associated acne. The natural skin tone had returned to the affected areas and the subject had sufficient confidence to leave her house without the having first applied cosmetic coverage. The subject continued to apply the formulation twice daily and has now ceased the use of all other remedies including tetracycline.

Formulation X is phosphatidyl choline (64.5 mg/g) as a lipid, Tween 80 (35.5.429 mg/g) as a surfactant, phosphate buffer (pH 6.7), benzyl alcohol (5.3 mg/g)1, BHA (0.200 mg/g), sodium metabisulfite (0.500 mg/g), glycerol (30.000 mg/g), EDTA (3.000 mg/g), and ethanol (30.000 mg/g), carbopol gelling agent (10.0 mg/g) +water to total 1 g.

Example 4

A 64 year old female subject who had suffered for 15+ years with facial Rosacea had tried many and varied remedies including prescribed antibiotics. None of the remedies provided any relief and the subject had to apply cosmetics on a daily basis before any public appearance. The subject found almost immediate benefit from applying formulation X twice daily to the affected areas of the face. Within 2 weeks of twice daily applications the condition had been seen to subside. The normal skin tone had returned for the first time in 15+ years and the subject was confident to leave her home without having first applied cosmetic covering. The subject ceased any further medication including tetracyclines and with continued use of the formulation the condition has not returned.

Example 5

A 32 year old female had extensive facial rosacea for 5+ years which was permanently present but could be exacerbated by alcohol or cold weather. The subject managed the condition principally by heavy cosmetic coverage.

After applying formulation X twice daily for several days the condition had subsided. The subject immediately reduced the amount of cosmetic applied and was progressively more confident to reduce cosmetics to almost zero with a further 2 weeks of twice daily application of the formulation. Cold weather or alcohol now does not affect the condition of her skin, the rosacea has effectively been eliminated.

Example 6

A 42 year old male who had rosacea for 6 years and had consulted specialists and been prescribed antibiotics. No medicine or available treatment was seen to provide any benefit. He applied formulation X twice daily for one week and noticed immediate reduction in flushed appearance and the disappearance of associated acne. He continues to apply the formulation to the areas where flushing would be expected to appear and has experienced continued relief.

Example 7

A 49 year old female had facial rosacea (cheeks and nose areas) for approximately 3 years and had noticed progressive worsening of the condition and associated acne. Occasionally a small amount of blood would protrude from pores in the affected area. The condition was managed sub optimally with cosmetics. Formulation X was applied daily and the subject noticed almost immediate benefit. The flushed appearance diminished within two days and the acne had disappeared within a week. Continued use of the formulation ensures the condition does not return. However on occasion when the formulation has not been applied for a few days the condition can reappear. Resumption of the formulation daily use combats the condition and returns normal skin tone, absence of acne and pore bleeds.

The invention claimed is:

1. A method of treating rosacea, the method comprising:
    administering to a subject in need of treatment for rosacea, a vesicular formulation consisting of Example 96, Formula A and Formula X, wherein the formulations consist of:
    Example Formulation 96
        68 mg/g phosphatidylcholine;
        8.5 mg/g Tween 80;
        pH 7.5 phosphate buffer;
        0.2 mg/g BHT;
        0.5 mg/g sodium metabisulfite;
        5.2 mg/g benzyl alcohol;
        2.5 mg/g methyl paraben;
        2.5 mg/g ethyl paraben;
        30 mg/g glycerol;
        1 mg/g EDTA;
        1 mg/g Linalool;
        12.5 mg/g Carbopol;
        36 mg/g ethanol,
    and
    Formula A
        64.5 mg/g phosphatidylcholine;
        35.5 mg/g Tween 80;
        7.7 mg/g Disodium phosphate;
        4.4 mg/g Sodium phosphate
        0.2 mg/g BHA;
        5.2 mg/g benzyl alcohol;
        2.5 mg/g methyl paraben;
        1.7 mg/g ethyl paraben
        12.7 mg/g Tromethamine;
        30 mg/g glycerol;
        3 mg/g EDTA;
        1 mg/g Linalool;
        791.5 mg/g Aqua
        10 mg/g Carbomer;
        30 mg/g ethanol,
    and
    Formulation X
        64.5 mg/g phosphatidylcholine;
        35.5 mg/g Tween 80;
        pH 6.7 phosphate buffer;
        0.2 mg/g BHA;
        5.3 mg/g benzyl alcohol;
        0.5 mg/g sodium metabisulfite;
        30 mg/g glycerol;
        3 mg/g EDTA;
        821 mg/g Water
        10 mg/g Carbopol;
        30 mg/g ethanol.

2. The method of claim 1, wherein treating rosacea comprises treatment of erythema associated with rosacea.

3. The method of claim 1, wherein treating rosacea comprises treatment of thread veins associated with rosacea.

4. The method of claim 1, wherein the formulation is a cream, lotion, ointment, gel, solution, spray, lacquer or film forming solution.

5. The method of claim 1, wherein the treating comprises administering the formulation to the subject over a period of one or more weeks.

6. The method of claim 1, wherein the treating comprises administering to the subject a dose of the formulation of about 0.1 to about 10 grams.

7. The method of claim 1, wherein the subject is a human and the method results in an improvement in rating in the Rosacea Standard Grading System (RSGS) in the human compared to a baseline RSGS rating and the rating is measured by a Rosacea Quality Of Life instrument (R-QOL).

8. The method of claim 7, wherein the improvement in rating in RSGS is due to an improvement in features selected from the group consisting of flushing, nontransient erythema, papules and pustules, telangiectasia, burning or stinging, plaques, dry appearance, edema, ocular manifestations and phymatous.

9. The method of claim 7, wherein administration results in at least 25% reduction in the underlying redness of the rosacea or 25% reduction in appearance of thread veins.

10. The method of claim 8, wherein administration results in at least one grade improvement in features selected from the group consisting of flushing, nontransient erythema, and telangiectasia.

* * * * *